United States Patent
O'Farrell et al.

(10) Patent No.: US 9,599,615 B2
(45) Date of Patent: Mar. 21, 2017

(54) LATERAL FLOW ASSAYS USING TWO DIMENSIONAL TEST AND CONTROL SIGNAL READOUT PATTERNS

(71) Applicant: Symbolics, LLC, Irvine, CA (US)

(72) Inventors: Brendan O'Farrell, Irvine, CA (US); Thomas C. Tisone, Orange, CA (US)

(73) Assignee: Symbolics, LLC, Irvine, CA (US)

(*) Notice: Subject to any disclaimer, the term of this patent is extended or adjusted under 35 U.S.C. 154(b) by 134 days.

(21) Appl. No.: 14/485,283

(22) Filed: Sep. 12, 2014

(65) Prior Publication Data

US 2015/0080254 A1 Mar. 19, 2015

Related U.S. Application Data

(60) Provisional application No. 61/877,852, filed on Sep. 13, 2013.

(51) Int. Cl.
| | |
|---|---|
| G01N 33/558 | (2006.01) |
| G01N 33/543 | (2006.01) |
| B01L 3/00 | (2006.01) |

(52) U.S. Cl.
CPC ...... *G01N 33/54386* (2013.01); *B01L 3/5023* (2013.01); *G01N 33/558* (2013.01); *B01L 2200/148* (2013.01); *B01L 2300/028* (2013.01)

(58) Field of Classification Search
None
See application file for complete search history.

(56) References Cited

U.S. PATENT DOCUMENTS

| | | |
|---|---|---|
| 3,641,235 A | 2/1972 | Weiss |
| 3,959,078 A | 5/1976 | Guire |
| 3,966,897 A | 6/1976 | Renn et al. |
| 4,094,647 A | 6/1978 | Deutsch et al. |
| 4,168,146 A | 9/1979 | Grubb et al. |
| 4,299,916 A | 11/1981 | Litman et al. |
| 4,332,788 A | 6/1982 | Mochida et al. |
| 4,347,312 A | 8/1982 | Brown et al. |
| 4,366,241 A | 12/1982 | Tom et al. |
| 4,373,932 A | 2/1983 | Gribnau et al. |
| 4,391,904 A | 7/1983 | Litman et al. |
| 4,425,438 A | 1/1984 | Bauman et al. |
| 4,517,288 A | 5/1985 | Giegel et al. |
| 4,695,554 A | 9/1987 | O'Connell et al. |
| 4,703,017 A | 10/1987 | Campbell et al. |
| 4,743,560 A | 5/1988 | Campbell et al. |

(Continued)

FOREIGN PATENT DOCUMENTS

| | | |
|---|---|---|
| CN | 1800831 | 7/2006 |
| CN | 101151531 | 3/2008 |

(Continued)

OTHER PUBLICATIONS

Broach, et al., "High throughput screening for drug discovery," Nature (1996) 384:14-16.

(Continued)

*Primary Examiner* — Chris L Chin
(74) *Attorney, Agent, or Firm* — Morrison & Foerster LLP

(57) ABSTRACT

The present invention relates to novel lateral flow devices using two dimensional features, preferably, uniform two dimensional test and control signal readout patterns, and the methods for detecting an analyte using the lateral flow devices.

26 Claims, 2 Drawing Sheets

This is what is printed. The box around the N is a field of capture reagent. This could be a solid field of spots or a feature that makes this N into a symbol or an unintelligible feature If analyte is present, the P and S appear, and the N is obscured. The O appears as control.

If analyte is not present, the P and S do not appear, and the N appears. The O appears as control.

(56) References Cited

U.S. PATENT DOCUMENTS

| | | |
|---|---|---|
| 4,778,751 A | 10/1988 | El Shami et al. |
| 4,857,453 A | 8/1989 | Ullman et al. |
| 4,861,711 A | 8/1989 | Friesen et al. |
| 4,956,302 A | 9/1990 | Gordon et al. |
| 4,960,691 A | 10/1990 | Gordon et al. |
| 5,073,484 A | 12/1991 | Swanson et al. |
| 5,075,078 A * | 12/1991 | Osikowicz ....... G01N 33/54366 422/420 |
| 5,079,142 A | 1/1992 | Coleman et al. |
| 5,120,643 A | 6/1992 | Ching et al. |
| 5,132,085 A * | 7/1992 | Pelanek ........... G01N 33/54366 422/402 |
| 5,141,875 A | 8/1992 | Kelton et al. |
| 5,160,701 A * | 11/1992 | Brown, III ........... G01N 33/521 422/408 |
| 5,236,826 A | 8/1993 | Marshall |
| 5,252,459 A | 10/1993 | Tarcha et al. |
| 5,252,496 A | 10/1993 | Kang et al. |
| 5,275,785 A | 1/1994 | May et al. |
| 5,378,638 A | 1/1995 | Deeg et al. |
| 5,401,667 A * | 3/1995 | Koike .................. G01N 33/558 422/412 |
| 5,422,726 A | 6/1995 | Tyler |
| 5,501,949 A | 3/1996 | Marshall |
| 5,504,013 A | 4/1996 | Senior |
| 5,514,602 A | 5/1996 | Brooks, Jr. et al. |
| 5,559,041 A | 9/1996 | Kang et al. |
| 5,571,726 A | 11/1996 | Brooks, Jr. et al. |
| 5,578,577 A | 11/1996 | Ching et al. |
| 5,591,645 A | 1/1997 | Rosenstein |
| 5,596,414 A | 1/1997 | Tyler |
| 5,602,040 A | 2/1997 | May et al. |
| 5,622,871 A | 4/1997 | May et al. |
| 5,654,162 A | 8/1997 | Guire et al. |
| 5,656,448 A | 8/1997 | Kang et al. |
| 5,656,503 A | 8/1997 | May et al. |
| 5,710,005 A | 1/1998 | Rittenburg |
| 5,712,170 A | 1/1998 | Kouvonen et al. |
| 5,714,389 A | 2/1998 | Charlton et al. |
| 5,716,778 A | 2/1998 | Weng et al. |
| 5,728,587 A | 3/1998 | Kang et al. |
| 5,747,273 A | 5/1998 | Khosravi et al. |
| 5,753,517 A | 5/1998 | Brooks et al. |
| 5,798,273 A | 8/1998 | Shuler et al. |
| 5,837,546 A | 11/1998 | Allen et al. |
| 5,869,252 A | 2/1999 | Bouma et al. |
| 5,915,386 A | 6/1999 | Lloyd et al. |
| 5,965,458 A | 10/1999 | Kouvonen et al. |
| 5,968,839 A | 10/1999 | Blatt et al. |
| 5,989,921 A | 11/1999 | Charlton et al. |
| 6,017,767 A | 1/2000 | Chandler |
| 6,020,147 A | 2/2000 | Guire et al. |
| 6,027,943 A | 2/2000 | Kang et al. |
| 6,077,222 A | 6/2000 | Lloyd et al. |
| 6,080,106 A | 6/2000 | Lloyd et al. |
| 6,100,099 A | 8/2000 | Gordon et al. |
| 6,103,536 A | 8/2000 | Geisberg |
| 6,121,008 A | 9/2000 | Fitzpatrick et al. |
| 6,140,048 A | 10/2000 | Muller et al. |
| 6,140,134 A | 10/2000 | Rittenburg |
| 6,156,271 A | 12/2000 | May |
| 6,186,962 B1 | 2/2001 | Lloyd et al. |
| 6,187,269 B1 | 2/2001 | Lancesseur et al. |
| 6,187,598 B1 | 2/2001 | May et al. |
| 6,194,222 B1 | 2/2001 | Buechler et al. |
| 6,210,898 B1 | 4/2001 | Bouma et al. |
| D441,298 S | 5/2001 | Gundlach et al. |
| 6,228,660 B1 | 5/2001 | May et al. |
| 6,241,862 B1 | 6/2001 | McAleer et al. |
| 6,267,722 B1 | 7/2001 | Anderson et al. |
| 6,287,875 B1 | 9/2001 | Geisberg |
| 6,319,665 B1 | 11/2001 | Zwanziger et al. |
| 6,319,676 B1 | 11/2001 | Nazareth et al. |
| 6,352,862 B1 | 3/2002 | Davis et al. |
| 6,368,875 B1 | 4/2002 | Geisberg |
| 6,379,620 B1 | 4/2002 | Tydings et al. |
| 6,394,952 B1 | 5/2002 | Anderson et al. |
| 6,399,398 B1 | 6/2002 | Cunningham et al. |
| 6,403,380 B1 | 6/2002 | Catt et al. |
| 6,406,920 B1 | 6/2002 | Davis et al. |
| 6,409,662 B1 | 6/2002 | Lloyd et al. |
| 6,451,619 B1 | 9/2002 | Catt et al. |
| 6,454,726 B1 | 9/2002 | Catt et al. |
| 6,485,982 B1 | 11/2002 | Charlton |
| 6,506,612 B2 | 1/2003 | Kang et al. |
| 6,534,320 B2 | 3/2003 | Ching et al. |
| 6,541,277 B1 | 4/2003 | Kang et al. |
| 6,544,797 B1 | 4/2003 | Buechler et al. |
| 6,551,495 B1 | 4/2003 | Porter et al. |
| 6,585,663 B1 | 7/2003 | Coley et al. |
| 6,649,418 B1 | 11/2003 | Geisberg |
| D484,600 S | 12/2003 | Kaar et al. |
| RE38,430 E | 2/2004 | Rosenstein |
| 6,706,049 B2 | 3/2004 | Moerman |
| 6,707,554 B1 | 3/2004 | Miltner et al. |
| 6,719,923 B2 | 4/2004 | Stiene et al. |
| 6,737,277 B1 | 5/2004 | Kang et al. |
| 6,759,202 B2 | 7/2004 | Grossman et al. |
| 6,764,827 B1 | 7/2004 | Aoki et al. |
| 6,766,817 B2 | 7/2004 | da Silva |
| 6,767,709 B1 | 7/2004 | Suzuki et al. |
| 6,770,487 B2 | 8/2004 | Crosby |
| 6,777,198 B2 | 8/2004 | Mendel-Hartvig et al. |
| D497,673 S | 10/2004 | Long |
| 6,805,837 B2 | 10/2004 | Tydings |
| 6,805,838 B2 | 10/2004 | Tydings |
| D497,999 S | 11/2004 | Long |
| 6,812,038 B1 | 11/2004 | Mendel-Hartvig et al. |
| 6,818,455 B2 | 11/2004 | May et al. |
| 6,830,731 B1 | 12/2004 | Buechler et al. |
| 6,849,450 B2 | 2/2005 | Langley et al. |
| 6,861,214 B1 | 3/2005 | Rampal et al. |
| 6,867,051 B1 | 3/2005 | Anderson et al. |
| 6,916,666 B1 | 7/2005 | Mendel-Hartvig et al. |
| 6,927,064 B1 | 8/2005 | Catt et al. |
| 6,936,476 B1 | 8/2005 | Anderson et al. |
| D509,901 S | 9/2005 | Phelan et al. |
| D510,711 S | 10/2005 | Syme et al. |
| 6,951,631 B1 | 10/2005 | Catt et al. |
| 7,049,150 B2 | 5/2006 | Bachand |
| D523,964 S | 6/2006 | Phelan et al. |
| 7,081,348 B2 | 7/2006 | Suzuki et al. |
| 7,096,877 B2 | 8/2006 | Larsen et al. |
| 7,109,042 B2 | 9/2006 | May et al. |
| D530,825 S | 10/2006 | Lee et al. |
| D531,735 S | 11/2006 | Lee et al. |
| 7,138,269 B2 | 11/2006 | Blankenstein |
| 7,141,212 B2 | 11/2006 | Catt et al. |
| 7,153,651 B1 | 12/2006 | Drewes et al. |
| 7,153,681 B1 | 12/2006 | Penfold et al. |
| D536,798 S | 2/2007 | Lee et al. |
| 7,175,992 B2 | 2/2007 | Fong |
| 7,178,416 B2 | 2/2007 | Whelan et al. |
| 7,205,553 B2 | 4/2007 | Dorsel et al. |
| RE39,664 E | 5/2007 | Gordon et al. |
| 7,226,752 B1 | 6/2007 | Roitman |
| 7,238,537 B2 | 7/2007 | Davis et al. |
| 7,238,538 B2 | 7/2007 | Freitag et al. |
| 7,239,394 B2 | 7/2007 | Sharrock et al. |
| 7,244,392 B1 | 7/2007 | Konecke |
| 7,247,500 B2 | 7/2007 | Wei et al. |
| 7,256,053 B2 | 8/2007 | Hu |
| 7,270,970 B2 | 9/2007 | Anderson et al. |
| 7,280,201 B2 | 10/2007 | Helbing |
| 7,297,502 B2 * | 11/2007 | Gao .................. G01N 33/558 422/402 |
| D557,815 S | 12/2007 | Lee et al. |
| 7,305,896 B2 | 12/2007 | Howell et al. |
| 7,312,027 B2 | 12/2007 | Bachand |
| 7,315,378 B2 | 1/2008 | Phelan et al. |
| 7,317,532 B2 | 1/2008 | Sharrock et al. |
| 7,323,139 B2 | 1/2008 | LaBorde et al. |
| 7,371,582 B2 | 5/2008 | Nahm et al. |
| D570,490 S | 6/2008 | Laverack |

(56) References Cited

U.S. PATENT DOCUMENTS

| | | | |
|---|---|---|---|
| D571,019 S | 6/2008 | Laverack |
| D571,020 S | 6/2008 | Laverack |
| 7,384,796 B2 | 6/2008 | Davis et al. |
| 7,391,512 B2 | 6/2008 | Fouquet et al. |
| D574,966 S | 8/2008 | Laverack |
| D575,876 S | 8/2008 | Laverack |
| D575,877 S | 8/2008 | Laverack |
| 7,407,813 B2 | 8/2008 | Davis et al. |
| 7,410,768 B2 | 8/2008 | Butlin et al. |
| 7,416,700 B2 | 8/2008 | Buechler et al. |
| D576,737 S | 9/2008 | Lee |
| 7,437,913 B2 | 10/2008 | Djennati et al. |
| 7,438,852 B2 | 10/2008 | Tung et al. |
| 7,459,314 B2 | 12/2008 | Guo et al. |
| 7,459,317 B2 | 12/2008 | Roitman |
| 7,476,549 B2 | 1/2009 | Nahm et al. |
| 7,510,881 B2 | 3/2009 | Ramael et al. |
| 7,516,845 B2 | 4/2009 | Lang et al. |
| 7,517,495 B2 | 4/2009 | Wu et al. |
| 7,521,259 B2 | 4/2009 | Petruno et al. |
| 7,521,560 B2 | 4/2009 | Li et al. |
| 7,522,762 B2 | 4/2009 | Rea et al. |
| 7,526,485 B2 | 4/2009 | Hagan et al. |
| D592,759 S | 5/2009 | Laverack |
| 7,532,128 B2 | 5/2009 | Petrilla |
| 7,534,393 B2 | 5/2009 | Catt et al. |
| 7,553,630 B2 | 6/2009 | Langley et al. |
| D597,216 S | 7/2009 | McGuigan et al. |
| 7,588,908 B2 | 9/2009 | Buechler et al. |
| 7,591,791 B2 | 9/2009 | Keren |
| D602,599 S | 10/2009 | Xiaowei |
| 7,616,315 B2 | 11/2009 | Sharrock et al. |
| 7,625,763 B2 | 12/2009 | Panotopoulos |
| 7,629,178 B2 | 12/2009 | Davis et al. |
| 7,632,460 B2 | 12/2009 | Catt et al. |
| 7,633,620 B2 | 12/2009 | Nahm et al. |
| 7,662,643 B2 | 2/2010 | Wei et al. |
| 7,679,745 B2 | 3/2010 | Claps et al. |
| 7,691,595 B2 | 4/2010 | Fong |
| 7,704,702 B2 | 4/2010 | Keren et al. |
| 7,704,753 B2 * | 4/2010 | Tang .................. G01N 33/558 422/402 |
| 7,705,976 B2 | 4/2010 | Robrish |
| 7,713,703 B1 | 5/2010 | Buechler et al. |
| 7,718,443 B2 | 5/2010 | Beesley et al. |
| D617,468 S | 6/2010 | Marquordt et al. |
| 7,741,103 B2 | 6/2010 | Guirguis |
| 7,763,454 B2 | 7/2010 | Nazareth et al. |
| 7,763,475 B2 | 7/2010 | Klenerman et al. |
| D621,059 S | 8/2010 | Marquordt et al. |
| 7,775,976 B2 | 8/2010 | Fuller et al. |
| 7,784,678 B2 | 8/2010 | Kuo et al. |
| 7,785,899 B2 | 8/2010 | Saul et al. |
| 7,796,266 B2 | 9/2010 | Cohen et al. |
| 7,799,554 B2 | 9/2010 | Mazumdar et al. |
| 7,803,636 B2 | 9/2010 | Gao et al. |
| 7,815,853 B2 | 10/2010 | Nahm et al. |
| 7,815,854 B2 | 10/2010 | Cohen |
| 7,819,822 B2 | 10/2010 | Calasso et al. |
| 7,838,258 B2 | 11/2010 | Yang et al. |
| 7,842,472 B2 | 11/2010 | Valkirs et al. |
| 7,858,396 B2 | 12/2010 | Corstjens et al. |
| 7,863,268 B2 | 1/2011 | Makarov et al. |
| 7,873,939 B2 | 1/2011 | Tian et al. |
| 7,879,624 B2 | 2/2011 | Sharrock |
| 7,879,979 B2 | 2/2011 | Buechler et al. |
| D634,023 S | 3/2011 | Wei |
| D634,620 S | 3/2011 | Edwards |
| D634,621 S | 3/2011 | Edwards |
| 7,901,949 B2 | 3/2011 | Raj |
| 7,910,309 B2 | 3/2011 | Cary et al. |
| 7,925,445 B2 | 4/2011 | Petrilla et al. |
| 7,939,342 B2 | 5/2011 | Song et al. |
| D639,976 S | 6/2011 | Francis et al. |
| D639,977 S | 6/2011 | Francis et al. |
| D640,389 S | 6/2011 | Francis et al. |
| 7,980,149 B2 | 7/2011 | Godfrey et al. |
| 7,985,560 B2 | 7/2011 | Valkirs et al. |
| 8,017,339 B2 | 9/2011 | Piepenburg et al. |
| 8,022,194 B2 | 9/2011 | Piepenburg et al. |
| 8,024,148 B2 | 9/2011 | Petruno et al. |
| 8,029,982 B2 | 10/2011 | Kingsmore et al. |
| 8,030,000 B2 | 10/2011 | Piepenburg et al. |
| 8,038,965 B2 | 10/2011 | Keren |
| 8,039,783 B2 | 10/2011 | Lai |
| 8,043,867 B2 | 10/2011 | Petruno et al. |
| 8,062,850 B2 | 11/2011 | Piepenburg et al. |
| 8,062,901 B2 | 11/2011 | Dai et al. |
| 8,071,308 B2 | 12/2011 | Piepenburg et al. |
| 8,071,394 B2 | 12/2011 | Wu et al. |
| 8,084,224 B2 | 12/2011 | Buechler et al. |
| 8,114,612 B2 | 2/2012 | Buechler et al. |
| 8,128,871 B2 | 3/2012 | Petruno et al. |
| 8,129,191 B2 | 3/2012 | Sheard et al. |
| 8,153,381 B2 | 4/2012 | Palin et al. |
| D659,847 S | 5/2012 | Li |
| 8,486,717 B2 * | 7/2013 | O'Farrell .............. G01N 33/558 422/400 |
| 2003/0073121 A1 * | 4/2003 | Mendel-Hartvig .. C12Q 1/6834 435/6.19 |
| 2003/0119202 A1 | 6/2003 | Kaylor et al. |
| 2005/0221504 A1 | 10/2005 | Petruno et al. |
| 2005/0221505 A1 | 10/2005 | Petruno et al. |
| 2005/0244953 A1 | 11/2005 | Cohen |
| 2006/0019265 A1 | 1/2006 | Song et al. |
| 2006/0172438 A1 | 8/2006 | Milunic et al. |
| 2006/0199278 A1 | 9/2006 | Leclipteux et al. |
| 2006/0223193 A1 | 10/2006 | Song et al. |
| 2006/0240541 A1 | 10/2006 | Petruno et al. |
| 2007/0048807 A1 | 3/2007 | Song |
| 2007/0141696 A1 | 6/2007 | Baugh et al. |
| 2007/0143035 A1 | 6/2007 | Petruno |
| 2007/0185679 A1 | 8/2007 | Petruno et al. |
| 2007/0211965 A1 | 9/2007 | Helbing et al. |
| 2008/0028261 A1 | 1/2008 | Petruno et al. |
| 2008/0069732 A1 | 3/2008 | Yi et al. |
| 2009/0047673 A1 | 2/2009 | Cary |
| 2009/0117006 A1 | 5/2009 | Fernandez |
| 2009/0157023 A1 | 6/2009 | Song et al. |
| 2009/0180925 A1 | 7/2009 | Petruno et al. |
| 2009/0180926 A1 | 7/2009 | Petruno et al. |
| 2009/0180927 A1 | 7/2009 | Petruno et al. |
| 2009/0180928 A1 | 7/2009 | Petruno et al. |
| 2009/0180929 A1 | 7/2009 | Petruno et al. |
| 2009/0214383 A1 | 8/2009 | Petruno et al. |
| 2009/0269858 A1 | 10/2009 | Punyadeera et al. |
| 2009/0311724 A1 | 12/2009 | Levison et al. |
| 2009/0325201 A1 | 12/2009 | Franzmann et al. |
| 2010/0015611 A1 | 1/2010 | Webster et al. |
| 2010/0081148 A1 | 4/2010 | Singbartl et al. |
| 2010/0094564 A1 | 4/2010 | Kuo et al. |
| 2010/0143941 A1 | 6/2010 | Wu et al. |
| 2010/0165338 A1 | 7/2010 | Claps |
| 2010/0173423 A1 | 7/2010 | Zuaretz et al. |
| 2010/0239460 A1 | 9/2010 | Nazareth et al. |
| 2010/0240149 A1 | 9/2010 | Nazareth et al. |
| 2010/0255510 A1 | 10/2010 | Wang et al. |
| 2010/0279301 A1 | 11/2010 | Chinnaiyan et al. |
| 2010/0311181 A1 | 12/2010 | Abraham et al. |
| 2011/0003398 A1 | 1/2011 | Mendel-Hartvig et al. |
| 2011/0011959 A1 | 1/2011 | Greenwood et al. |
| 2011/0065136 A1 | 3/2011 | Labrie et al. |
| 2011/0065137 A1 | 3/2011 | LaBrie et al. |
| 2011/0065593 A1 | 3/2011 | Labrie et al. |
| 2011/0065598 A1 | 3/2011 | Labrie et al. |
| 2011/0065599 A1 | 3/2011 | LaBrie et al. |
| 2011/0065608 A1 | 3/2011 | LaBrie et al. |
| 2011/0124519 A1 | 5/2011 | Falkenberg et al. |
| 2011/0171754 A1 | 7/2011 | Redmond et al. |
| 2012/0142023 A1 | 6/2012 | Ascoli et al. |
| 2012/0184462 A1 | 7/2012 | O'Farrell et al. |

(56) References Cited

U.S. PATENT DOCUMENTS

| 2013/0225448 A1 | 8/2013 | O'Farrell et al. |
|---|---|---|
| 2013/0225449 A1 | 8/2013 | O'Farrell et al. |

FOREIGN PATENT DOCUMENTS

| DE | 10 2006 060 066 | | 6/2007 | |
|---|---|---|---|---|
| DE | 10 2007 010 757 | | 9/2007 | |
| DE | 10 2007 044 889 | | 4/2008 | |
| EP | 0 149 168 | | 7/1985 | |
| EP | 0 250 137 | | 12/1987 | |
| EP | 0 323 605 | | 7/1989 | |
| EP | 1 459 068 | | 9/2004 | |
| EP | 1 582 598 | | 10/2005 | |
| EP | 1 666 879 | | 6/2006 | |
| EP | 2 666 018 | | 11/2013 | |
| GB | 1 526 708 | | 9/1978 | |
| WO | WO-99/40438 | | 8/1999 | |
| WO | WO-03/058242 | | 7/2003 | |
| WO | WO 03058242 | A2 * | 7/2003 | ....... G01N 33/54386 |
| WO | WO-2005/073733 | | 8/2005 | |
| WO | WO-2008/084331 | | 7/2008 | |
| WO | WO-2012/099897 | | 7/2012 | |
| WO | WO-2015/038978 | | 3/2015 | |

OTHER PUBLICATIONS

Burbaum et al., "New technologies for high-throughput screening," Curr Opin Chem Biol. (1997) 1:72-78.
Carter et al., "Lateral flow microarrays: a novel platform for rapid nucleic acid detection based on miniaturized lateral flow chromatography," Nucleic Acids Research (2007) 35(10):e74.
Communication pursuant to Rule 114(2) EPC for Application No. 12 709 406.8 dated Dec. 1, 2015.
Communication pursuant to Article 94(3) EPC for EP 12709406.8, mailed Apr. 20, 2015, 5 pages.
Communication pursuant to Article 94(3) EPC for EP 12 709 406.8, mailed Apr. 18, 2016, 3 pages.
Dictionary definition of "adjacent", Merriam-Webster Online Dictionary (www.mw.com/dictionary/adjacent), dated Nov. 22, 2005.
E-mail from Elson Silva dated Jul. 19, 2012, 7 pages.
Examination Report in European Patent Application No. EP12709406.8, dated Jul. 16, 2014, 5 pages.
Fernandes et al., "Letter from the society president," J. Biomol. Screening (1997) 2:1.
First Office Action in Chinese Patent Application No. 201280005790.1, dated Oct. 15, 2014, 18 pages (English language summary included).
Gantelius et al., "A lateral flow protein microarray for rapid determination of contagious bovine pleuropneumonia status in bovine serum," J Microbiol Methods (2010) 82(1):11-8.
Harlow et al., "Using Antibodies: A Laboratory Manual," p. 8 (Cold Spring Harbor Laboratory Press, Cold Springs Harbor, New York, 1999).
Invitation Pursuant to Rule 137(4) EPC in European Patent Application No. EP12709406.8, dated May 21, 2014, 2 pages.
Illustration from Weiss Patent (US Pat. No. 3,6431,235).
"Immunoglobulin D", Wikipedia, the free encyclopedia (en.wikipedia.org/wiki/IgD), dated Feb. 6, 2011.
"Immunoglobulin G", Wikipedia, the free encyclopedia (en.wikipedia.org/wiki/IgG), dated Feb. 6, 2011.
International Preliminary Report on Patentability for PCT/US14/55520, mailed Sep. 30, 2015, 5 pages.
International Preliminary Report on Patentability for PCT/US12/21586, mailed Mar. 29, 2013.
International Preliminary Report on Patentability in PCT/US2013/050952, mailed Aug. 28, 2014, 10 pages.
International Preliminary Report on Patentability for PCT/US2014/055520, mailed Dec. 1, 2014.
International Search Report and Written Opinion for PCT/US2012/021586, mailed Apr. 19, 2012, 8 pages.
International Search Report and Written Opinion for PCT/US2012047493, mailed Oct. 1, 2012, 16 pages.
International Search Report and Written Opinion for PCT/US2012/047497, mailed Oct. 15, 2012, 12 pages.
International Search Report and Written Opinion for PCT/US2013/050952, mailed Oct. 17, 2013, 12 pages.
International Search Report and Written Opinion for PCT/US2014/055520, mailed Dec. 1, 2014, 11 pages.
Janzen et al., "High throughput Screening as a Discovery Tool in the Pharmaceutical Industry," Lab Robotics Automation (1996) (8):261-265.
Leuvering et al., "Sole Particle Immunossay (SPIA)," J. Immunoassay (1980) 1(1):77-91.
Lexsee 365 F.2D 834, in re Griswold and Pearce, 365 F.2d 834 (1966).
Lexsee 417 F.3E 1369, *Pharmacia Corp.* v. *PAR Pharmaceutical, Inc.*, 417 F.3d 1369 (2005).
Notice of First Office Action for CN 1608207A for Application No. 201380046764.8, issued Oct. 10, 2015.
Notification of Granting Patent Right (translation) for CN 201280005790.1, issued Nov. 3, 2015, 2 pages.
Office Action in European Patent Application No. EP12709406.8, dated Sep. 6, 2013, 2 pages.
Office Action issued in U.S. Appl. No. 13/343,681, dated Aug. 20, 2012, 11 pages.
Office Action for U.S. Appl. No. 13/802,036, issued Jun. 27, 2016, 25 pages.
Office Action for U.S. Appl. No. 13/862,301, issued Jun. 30, 2016, 13 pages.
Office Action for U.S. Appl. No. 13/862,313, issued Jul. 1, 2016, 13 pages.
Request for Reexamination and Exhibits 1-5 for U.S. Pat. No. 6,805,837, dated Nov. 23, 2005.
Request for Reexamination and Exhibits 1-5 for U.S. Pat. No. 6,805,838, dated Nov. 23, 2005.
Request for Reexamination and Exhibits 1-3 for U.S. Pat. No. 5,073,484 dated Sep. 26, 2003.
Request for Reexamination and Exhibits 1-8 for U.S. Pat. No. 6,485,982 dated Sep. 15, 2005.
Requestor's Reply to Patent Owner's Statement and Exhibits 1-2 for U.S. Pat. No. 6,805,837, dated Feb. 22, 2006.
Requestor's Reply to Patent Owner's Statement and Exhibits 1-2 for U.S. Pat. No. 6,805,838, dated Feb. 22, 2006.
Restriction Requirement issued in U.S. Appl. No. 13/343,681, dated Apr. 9, 2012, 6 pages.
Response to Restriction Requirement in U.S. Appl. No. 13/343,681, dated Apr. 27, 2012, 9 pages.
Response to Communication pursuant to Art. 94(3) EPC for EP 12 709 406.8, filed Oct. 30, 2015, 10 pages.
Response to Office Action in European Patent Application No. EP12709406.8, dated Mar. 14, 2014, 7 pages.
Response to Written Opinion with Chapter II Demand and Article 34 Amendments in PCT/US2013/050952, dated May 19, 2014, 17 pages.
Response to Rule 137(4) EPC in European Patent Application No. EP12709406.8, dated Jun. 30, 2014, 3 pages.
Response to Office Action in U.S. Appl. No. 13/343,681, dated Apr. 12, 2013, 8 pages.
Response to the First Office Action for CN 201280005790.1, filed Mar. 30, 2015, 27 pages.
Response to Written Opinion for PCT/US2014/055520, filed Jul. 13, 2015, 26 pages.
Response to Office Action for CN 2013800467648, filed Feb. 25, 2016, 11 pages.
Response pursuant to the Communication pursuant to Article 94(3) EPC for EP 12 709 406.8, filed Jun. 27, 2016, 71 pages.
Response to Second Office Action for CN 201380046764.8, filed Sep. 9, 2016, 9 pages.
Second Office Action (translation) for CN 201280005790.1, issued May 27, 2015, 3 pages.
Second Office Action (translation) for CN 201380046764.8, issued May 26, 2016, 3 pages.

(56) References Cited

OTHER PUBLICATIONS

Statement by Patent Owner and Exhibits A-D for U.S. Pat. No. 6,805,837, dated Dec. 23, 2005.
Statement by Patent Owner and Exhibits A-D for U.S. Pat. No. 6,805,838, dated Dec. 23, 2005.
Summons to attend oral proceedings pursuant to rule 115(1) EPC for Application No. 12 709 406.8, dated Dec. 10, 2015.
Taranova et al., "Integration of lateral flow and microarray technologies for multiplex immunoassay: application to the determination of drugs of abuse," Microchim Acta (2013) 180:1165-1172.
Takeda et al., "Experience in Use of Urotrace for Urine of Patients," Rinsho Kensa (Clinical Test) (1974) (original article in Japanese followed by English translation).
ThermoFisher Scientific information sheet entitled "Color-Rich™ Fluoro-Max™ Dyed Microparticles," dated Mar. 2008.
Thermo Scientific Instructions sheet entitled Dylight™ Microscale Antibody Labeling Kits,: copyrighted 2010.
Van Hell et al., in Alternative Immunoassays (W.P. Collins ed., John Wiley & Sons, 1985), Ch. 4 "Particle Immunoassays," pp. 39-59.
Wood et al., "Base composition-independent hybridization in tetramethylammonium chloride: a method for oligonucleotide screening of highly complex gene libraries," Proc Natl Acad Sci USA (1985) 82(6):1585-1588.

* cited by examiner

LATERAL FLOW ASSAYS USING TWO DIMENSIONAL TEST AND CONTROL SIGNAL READOUT PATTERNS

I. CROSS-REFERENCE TO RELATED APPLICATIONS

This application claims the priority benefit of U.S. provisional application Ser. No. 61/877,852, filed Sep. 13, 2013, entitled "LATERAL FLOW ASSAYS USING TWO DIMENSIONAL TEST AND CONTROL SIGNAL READOUT PATTERNS." In some aspects, this application relates to U.S. Pat. No. 8,486,717, entitled "LATERAL FLOW ASSAYS USING TWO DIMENSIONAL FEATURES," International Application No. PCT/US2012/021586, filed Jan. 17, 2012, entitled "LATERAL FLOW ASSAYS USING TWO DIMENSIONAL FEATURES," U.S. application Ser. No. 13/802,036, filed Mar. 13, 2013, entitled "LATERAL FLOW ASSAYS USING TWO DIMENSIONAL FEATURES," and International Patent Application No. PCT/US2013/050952, filed Jul. 17, 2013, entitled "LATERAL FLOW ASSAYS USING TWO DIMENSIONAL FEATURES." The contents of the above referenced patent and applications are herein incorporated by reference in their entireties.

II. TECHNICAL FIELD

The present invention relates to novel lateral flow devices using two dimensional features, preferably, uniform two dimensional test and control signal readout patterns, and the methods for detecting an analyte using the lateral flow devices.

III. DISCLOSURE OF THE INVENTION

In one aspect, the present disclosure provides for a test device for detecting an analyte in a liquid sample, which device comprises a plurality of reagent dots on a matrix, wherein at least two of said reagent dots do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, and: 1) after a liquid sample containing no analyte or an analyte below detection level flows laterally along said test device and passes said plurality of reagent dots, said plurality of reagent dots form two separate two-dimensional signal features A and B, and said feature A, feature B or a combination thereof, viewed from a direction substantially parallel or opposite to the liquid sample flow direction, indicates that a test is properly conducted and said sample contains no analyte or the analyte below detection level; or 2) after a liquid sample containing an analyte at or above detection level flows laterally along said test device and passes said plurality of reagent dots, said plurality of reagent dots: a) form one discernible feature that is one of said features A and B, form additional signal feature C that obscures the other of said features A and B to form an obscured feature D, and said discernible feature from features A and B or a combination of said discernible feature from features A and B and said obscured feature D, viewed from a direction substantially parallel or opposite to the liquid sample flow direction, indicates that a test is properly conducted; and b) form at least one additional two-dimensional signal feature E, and a combination of said discernible feature from features A and B and said feature E, viewed from a direction substantially perpendicular to the liquid sample flow direction, indicates that said sample contains said analyte at or above detection level.

In another aspect, the present disclosure provides for a test device for detecting an analyte in a liquid sample, which device comprises a plurality of reagent dots on a matrix, wherein at least two of said reagent dots do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, and: 1) after a liquid sample containing no analyte or an analyte below detection level flows laterally along said test device and passes said plurality of reagent dots, said plurality of reagent dots form two separate two-dimensional signal features A and B, said feature A, feature B or a combination thereof, viewed from a direction substantially parallel or opposite to the liquid sample flow direction, indicates that a test is properly conducted and said sample contains no analyte or the analyte below detection level; or 2) after a liquid sample containing an analyte at or above detection level flows laterally along said test device and passes said plurality of reagent dots, said plurality of reagent dots: a) form two separate two-dimensional signal features A and B and an additional signal feature C, said feature A, feature B or a combination thereof, viewed from a direction substantially parallel or opposite to the liquid sample flow direction, indicates that a test is properly conducted, and a combination of one or both of said features A and B and said feature C, viewed from a direction substantially parallel or opposite to the liquid sample flow direction, generates a signal that aids interpretation of the test result; and b) form at least one additional two-dimensional signal feature E, and a combination of at least one of said features A and B and said feature E, viewed from a direction substantially perpendicular to the liquid sample flow direction, indicates that said sample contains said analyte at or above detection level.

In still another aspect, the present disclosure provides for a method for detecting an analyte in a liquid sample, which method comprises: a) contacting a liquid sample with any of the test devices descried above, wherein the liquid sample is applied to a site of the test device upstream of the plurality of reagent dots; b) transporting an analyte, if present in the liquid sample, and a labeled reagent to the plurality of reagent dots; and c) assessing the presence, absence, amount and/or pattern of signal(s) generated by the labeled reagent at the plurality of reagent dots to determining the presence, absence and/or amount of the analyte in the liquid sample.

The principles of the present test devices and methods can be applied, or can be adapted to apply, to the lateral flow test devices and assays known in the art. For example, the principles of the present test devices and methods can be applied, or can be adapted to apply, to the lateral flow test devices and assays disclosed and/or claimed in the U.S. Pat. Nos. 3,641,235, 3,959,078, 3,966,897, 4,094,647, 4,168, 146, 4,299,916, 4,347,312, 4,366,241, 4,391,904, 4,425,438, 4,517,288, 4,960,691, 5,141,875, 4,857,453, 5,073,484, 4,695,554, 4,703,017, 4,743,560, 5,075,078, 5,591,645, 5,656,448, RE 38,430 E, 5,602,040, 6,017,767, 6,319,676, 6,352,862, 6,485,982, 5,120,643, 4,956,302, RE 39,664 E, 5,252,496, 5,514,602, 7,238,538 B2, 7,175,992 B2, 6,770, 487 B2, 5,712,170, 5,275,785, 5,504,013, 6,156,271, 6,187, 269, 6,399,398, 7,317,532, EP 0,149,168 A1, EP 0,323,605 A1, EP 0,250,137 A2, GB 1,526,708 and WO99/40438.

IV. BRIEF DESCRIPTION OF THE DRAWINGS

V. DETAILED DESCRIPTION OF THE INVENTION

A. Definitions

Figure 1:
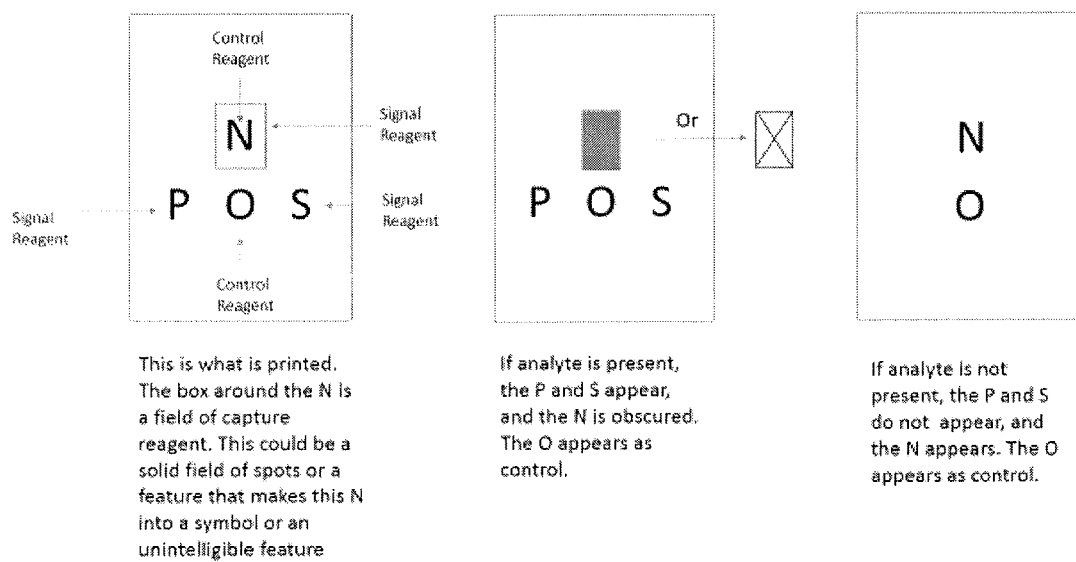
FIG. 1 illustrates an exemplary lateral flow test format using two dimensional test and control signal readout patterns.

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "the line is substantially parallel to the liquid sample flow direction" means that the angle between the line and the liquid sample flow direction is at least less than 45 degrees or more than 135 degrees. In some specific embodiments, the angle between the line and the liquid sample flow direction is at about 40, 35, 30, 25, 20, 15, 10, 5, 4, 3, 2, or 1 degree, or the line is completely parallel to the liquid sample flow direction. In other specific embodiments, the angle between the line and the liquid sample flow direction is at about 140, 145, 150, 155, 160, 165, 170, 175, 176, 177, 178, or 179 degrees, or the line is completely parallel to the liquid sample flow direction.

As used herein, "viewed from a direction substantially parallel or opposite to the liquid sample flow direction" means that the angle between the viewing direction and the liquid sample flow direction is at least less than 45 degrees or more than 135 degrees. In some specific embodiments, the angle between the viewing direction and the liquid sample flow direction is at about 40, 35, 30, 25, 20, 15, 10, 5, 4, 3, 2, or 1 degree, or the viewing direction is completely parallel to the liquid sample flow direction. In other specific embodiments, the angle between the viewing direction and the liquid sample flow direction is at about 140, 145, 150, 155, 160, 165, 170, 175, 176, 177, 178, or 179 degrees, or the viewing direction is completely opposite to the liquid sample flow direction.

As used herein, "the line is substantially perpendicular to the liquid sample flow direction" means that the angle between the line and the liquid sample flow direction is at least more than 45 degrees or less than 135 degrees. In some specific embodiments, the angle between the line and the liquid sample flow direction is at about 50, 55, 60, 65, 70, 75, 80, 85, 86, 87 88 or 89 degrees, or the line is completely perpendicular to the liquid sample flow direction. In other specific embodiments, the angle between the line and the liquid sample flow direction is at about 130, 125, 120, 115, 110, 105, 100, 95, 94, 93, 92 or 91 degrees, or the line is completely perpendicular to the liquid sample flow direction.

As used herein, "viewed from a direction substantially perpendicular to the liquid sample flow direction" means that the angle between the viewing direction and the liquid sample flow direction is at least more than 45 degrees or less than 135 degrees. In some specific embodiments, the angle between the viewing direction and the liquid sample flow direction is at about 50, 55, 60, 65, 70, 75, 80, 85, 86, 87 88 or 89 degrees, or the viewing direction is completely perpendicular to the liquid sample flow direction. In other specific embodiments, the angle between the viewing direction and the liquid sample flow direction is at about 130, 125, 120, 115, 110, 105, 100, 95, 94, 93, 92 or 91 degrees, or the viewing direction is completely perpendicular to the liquid sample flow direction.

As used herein, "reagent dots have substantially the same size or diameter" means that the difference in the size or diameter between the largest dot and smallest dot is not more than one fold or less than 50% of the average or median size or diameter of the reagent dots. In some specific embodiments, the difference in the size or diameter between the largest dot and smallest dot is within 45%, 40%, 30%, 20%, 10%, 5%, or 1% of the average or median size or diameter of the reagent dots. In other specific embodiments, reagent dots have the same size or diameter.

As used herein, "the distance between reagent dots is substantially the same" means that the distance between or among reagent dots, often adjacent reagent dots, is within 50% variation of the average or median distance between or among reagent dots or adjacent reagent dots. In some specific embodiments, the distance between or among reagent dots or adjacent reagent dots is within 45%, 40%, 30%, 20%, 10%, 5%, or 1% variation of the average or median distance between or among reagent dots or adjacent reagent dots. In other specific embodiments, the distance between or among reagent dots is the same. Such space or distance can be measured by any suitable means. In some specific embodiments, the space or distance between or among reagent dots is measured as the space or distance between or among the edges of the reagent dots or adjacent reagent dots. In other specific embodiments, the space or distance between or among reagent dots is measured as the space or distance between or among the centers or effective centers of the reagent dots or adjacent reagent dots.

As used herein, a "binding reagent" refers to any substance that binds to target or analyte with desired affinity and/or specificity. Non-limiting examples of the binding reagent include cells, cellular organelles, viruses, particles, microparticles, molecules, or an aggregate or complex thereof, or an aggregate or complex of molecules. Exemplary binding reagents can be an amino acid, a peptide, a protein, e.g., an antibody or receptor, a nucleoside, a nucleotide, an oligonucleotide, a nucleic acid, e.g., DNA or RNA, a vitamin, a monosaccharide, an oligosaccharide, a carbohydrate, a lipid, an aptamer and a complex thereof.

As used herein, "antibody" includes not only intact polyclonal or monoclonal antibodies, but also fragments thereof (such as Fab, Fab', F(ab')$_2$, Fv), single chain (ScFv), a diabody, a multi-specific antibody formed from antibody fragments, mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class As used herein, "monoclonal antibody" refers to an antibody obtained from a population of substantially homogeneous antibodies, i.e., the antibodies comprising the population are identical except for possible naturally occurring mutations that are present in minor amounts. As used herein, a "monoclonal antibody" further refers to functional fragments of monoclonal antibodies.

As used herein, the term "specifically binds" refers to the specificity of a binding reagent, e.g., an antibody, such that it preferentially binds to a defined analyte or target. Recognition by a binding reagent or an antibody of a particular analyte or target in the presence of other potential targets is one characteristic of such binding. In some embodiments, a binding reagent that specifically binds to an analyte avoids binding to other interfering moiety or moieties in the sample to be tested.

As used herein the term "avoids binding" refers to the specificity of particular binding reagents, e.g., antibodies or antibody fragments. Binding reagents, antibodies or antibody fragments that avoid binding to a particular moiety generally contain a specificity such that a large percentage of the particular moiety would not be bound by such binding reagents, antibodies or antibody fragments. This percentage generally lies within the acceptable cross reactivity percentage with interfering moieties of assays utilizing the binding reagents or antibodies directed to detecting a specific target. Frequently, the binding reagents, antibodies or antibody fragments of the present disclosure avoid binding greater than about 90% of an interfering moiety, although higher percentages are clearly contemplated and preferred. For example, binding reagents, antibodies or antibody fragments of the present disclosure avoid binding about 91%, about 92%, about 93%, about 94%, about 95%, about 96%, about 97%, about 98%, about 99%, and about 99% or more of an interfering moiety. Less occasionally, binding reagents, antibodies or antibody fragments of the present disclosure avoid binding greater than about 70%, or greater than about 75%, or greater than about 80%, or greater than about 85% of an interfering moiety.

As used herein, "mammal" refers to any of the mammalian class of species. Frequently, the term "mammal," as used herein, refers to humans, human subjects or human patients.

As used herein, the term "subject" is not limited to a specific species or sample type. For example, the term "subject" may refer to a patient, and frequently a human patient. However, this term is not limited to humans and thus encompasses a variety of mammalian species.

As used herein the term "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "stringency" of nucleic acid hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Current Protocols in Molecular Biology (Ausubel et al. eds., Wiley Interscience Publishers, 1995); Molecular Cloning: A Laboratory Manual (J. Sambrook, E. Fritsch, T. Maniatis eds., Cold Spring Harbor Laboratory Press, 2d ed. 1989); Wood et al., *Proc. Natl. Acad. Sci. USA,* 82:1585-1588 (1985).

As used herein the term "isolated" refers to material removed from its original environment, and is altered from its natural state. For example, an isolated polypeptide could be coupled to a carrier, and still be "isolated" because that polypeptide is not in its original environment.

As used herein, "test substance (or candidate compound)" refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on a target is determined by the disclosed and/or claimed methods herein.

As used herein, high-throughput screening (HTS) refers to processes that test a large number of samples, such as samples of diverse chemical structures against disease targets to identify "hits" (see, e.g., Broach, et al., High throughput screening for drug discovery, *Nature,* 384:14-16 (1996); Janzen, et al., High throughput screening as a discovery tool in the pharmaceutical industry, *Lab Robotics Automation:* 8261-265 (1996); Fernandes, P. B., Letter from the society president, *J. Biomol. Screening,* 2:1 (1997); Burbaum, et al., New technologies for high-throughput screening, *Curr. Opin. Chem. Biol.,* 1:72-78 (1997)). HTS operations are highly automated and computerized to handle sample preparation, assay procedures and the subsequent processing of large volumes of data.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" refers to small prokaryotic organisms (linear dimensions of around 1 micron) with non-compartmentalized circular DNA and ribosomes of about 70S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to an obligate intracellular parasite of living but non-cellular nature, consisting of DNA or RNA and a protein coat. Viruses range in diameter from about 20 to about 300 nm Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

B. Lateral Flow Devices Using Two Dimensional Features

In one aspect, the present disclosure provides for a test device for detecting an analyte in a liquid sample, which device comprises a plurality of reagent dots on a matrix, wherein at least two of said reagent dots do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, and: 1) after a liquid sample containing no analyte or an analyte below detection level flows laterally along said test device and passes said plurality of reagent dots, said plurality of reagent dots form two separate two-dimensional signal features A and B, and said feature A, feature B or a combination thereof, viewed from a direction substantially parallel or opposite to the liquid sample flow direction, indicates that a test is properly conducted and said sample contains no analyte or the analyte below detection level; or 2) after a liquid sample containing an analyte at or above detection level flows laterally along said test device and passes said plurality of reagent dots, said plurality of reagent dots: a) form one discernible feature that is one of said features A and B, form additional signal feature C that obscures the other of said features A and B to form an obscured feature D, and said discernible feature from features A and B or a combination of said discernible feature from features A and B and said obscured feature D, viewed from a direction substantially parallel or opposite to the liquid sample flow direction, indicates that a test is properly conducted; and b) form at least one additional two-dimensional signal feature E, and a combination of said discernible feature from features A and B and said feature E, viewed from a direction substantially perpendicular to the liquid sample flow direction, indicates that said sample contains said analyte at or above detection level.

In another aspect, the present disclosure provides for a test device for detecting an analyte in a liquid sample, which device comprises a plurality of reagent dots on a matrix, wherein at least two of said reagent dots do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, and: 1) after a liquid sample containing no analyte or an analyte below detection level flows laterally along said test device and passes said plurality of reagent dots, said plurality of reagent dots form two separate two-dimensional signal features A and B, said feature A, feature B or a combination thereof, viewed from a direction substantially parallel or opposite to the liquid sample flow direction, indicates that a test is properly conducted and said sample contains no analyte or the analyte below detection level; or 2) after a liquid sample containing an analyte at or above detection level flows laterally along said test device and passes said plurality of reagent dots, said plurality of reagent dots: a) form two separate two-dimensional signal features A and B and an additional signal feature C, said feature A, feature B or a combination thereof, viewed from a direction substantially parallel or opposite to the liquid sample flow direction, indicates that a test is properly conducted, and a combination of one or both of said features A and B and said feature C, viewed from a direction substantially parallel or opposite to the liquid sample flow direction, generates a signal that aids interpretation of the test result; and b) form at least one additional two-dimensional signal feature E, and a combination of at least one of said features A and B and said feature E, viewed from a direction substantially perpendicular to the liquid sample flow direction, indicates that said sample contains said analyte at or above detection level.

Numerous variables can be considered to make the test device to ensure that the reagent dots do not overlap and are sufficiently spaced apart from each other so that liquid sample flow to, through and/or around one reagent dot or set of reagent dots does not substantially affect flow of the liquid sample flow to, through and/or around other reagent dot or other sets of reagent dots. And at the same time, the test device should comprise sufficient number of the reagent dots that can be used in generating signal readout to indicate presence, absence and/or amount of said analyte in said liquid sample. Exemplary variables that can be considered and/or adjusted in making the test device include the number of reagent dots, the size and/or shape of the reagent dots, e.g., whether the absolute size or the size relative to the size of the matrix, the types and amounts of the reagents located at the reagent dots, the spacing between or among a portion or all reagent dots on the test device, e.g., whether the absolute size of the spacing or the size of the spacing relative to the size of the matrix and/or the number of the reagent dots on the matrix, the orientation or position of the reagent dots relative to the liquid sample flow direction, the uniformity or variations of the sizes and/or shape among the reagent dots and the properties of the matrix, e.g., the material and/or porosity of the matrix, and/or the properties or composition of the solution in which the reagent is spotted. Some or all of these variables can be tested, adjusted or determined to make a test device that meets the intended test performance, e.g., meeting the intended or desired assay sensitivity and/or specificity.

In some specific embodiments, it can be determined that the reagent dots do overlap and are not sufficiently spaced apart from each other so that liquid sample flow to, through and/or around one reagent dot or set of reagent dots blocks or prevents flow of the liquid sample flow to, through and/or around other reagent dot or other sets of reagent dots. Some or all of these variables can then be adjusted so that the liquid sample flow blocking effect be reduced by at least 10%, and preferably by at least 20%, 30%, 40%, 50%, 60%, 70%, 80%, 90%, 95%, 96%, 97%, 98%, 99%, or 100%. In other specific embodiments, given a particular configuration, the liquid sample flow to, through and/or around other reagent dot or other sets of reagent dots can be determined. Some or all of these variables can then be adjusted so that the liquid sample flow to, through and/or around other reagent dot or other sets of reagent dots be increased by at least 10%, and preferably by at least 20%, 30%, 40%, 50%, 60%, 70%, 80%, 90%, 95%, 96%, 97%, 98%, 99%, or 100%. In other embodiments, some or all of these variables can then be adjusted so that the liquid sample flow to, through and/or around other reagent dot or other sets of reagent dots be increased by 1 fold, 2 folds, 3 folds, 4 folds, 5 folds 6 folds, 7 folds, 8 folds, 9 folds, 10 folds, or more.

The test device can comprise any suitable number of reagent dots. In one example, the test device comprises two reagent dots. In another example, the test device comprises more than two reagent dots, such as at least 3, 4, 5, 6, 7, 8, 9, 10, 50, 100, 500, 1,000, 5,000, 10,000 or more reagent dots.

Any suitable number, portion or all of the reagent dots in the test device can be sufficiently spaced apart from each other. For example, at least a quarter, a third, half or all reagent dots do not overlap and are sufficiently spaced apart from each other so that when the liquid sample flows laterally along the matrix, flow of the liquid sample to, through and/or around one of the reagent dots does not substantially affect flow of the liquid sample to, through and/or around the other reagent dots.

The predetermined pattern formed at the reagent dots can take any form, shape and/or pattern. For example, the predetermined pattern can be a line, multiple lines, a symbol, a geometric shape and an alpha-numeric shape, a regular shape, or a irregular shape, or a combination thereof. The exemplary regular shape can be a line, a circle, a rod, a square, a triangle, and a rectangle. The exemplary alpha-numeric shape can be a letter, a word, a number or a combination thereof.

When the predetermined pattern is in the form of a line or multiple lines, the line(s) can be at any suitable orientation or position relative to the liquid sample flow direction. In one example, the line(s) is substantially parallel to the liquid sample flow direction. In another example, the line(s) is substantially perpendicular to the liquid sample flow direction. In still another example, the predetermined pattern is in the form of multiple lines. The multiple lines can comprise at least a line that is substantially parallel to the liquid sample flow direction and at least a line that is substantially perpendicular to the liquid sample flow direction. In some embodiments, at least a quarter, a third, half of the lines are substantially parallel to the liquid sample flow direction. In other embodiments, at least a quarter, a third, half of the lines are substantially perpendicular to the liquid sample flow direction.

The test device can be used to detect a single analyte or multiple analytes in a liquid sample. In one example, the plurality of reagent dots in the test device comprises different reagents and the test device is used to detect multiple analytes in the liquid sample. In another example, the plurality of reagent dots in the test device comprises the same reagent and the test device is used to detect the amount of a single analyte in the liquid sample.

The reagent dots in the test device can comprise any suitable amount of the reagent(s). In one example, the plurality of reagent dot comprises the same amount of the reagent(s). In another example, the plurality of reagent dots comprises the different amounts of the reagent(s).

The reagent dots in the test device can have any suitable size(s). In one example, at least one of the reagent dots has a diameter of about 0.1-1 um, 1-10 um, 10-50 um, 51-100 um, 101-200 um, 201-300 um, 301-400 um, 401-500 um and 501-1000 um. In another example, at least a quarter, a third, half or all reagent dots have a diameter of about 0.1-1 um, 1-10 um, 10-50 um, 51-100 um, 101-200 um, 201-300 um, 301-400 um, 401-500 um or 501-1000 um. In still another example, at least one of the reagent dots has a diameter or surface area that is about 10%, 5%, 1%, 0.5%, 0.1%, 0.05%, 0.01%, 0.001% or smaller diameter or surface area of the length, width or surface area of the matrix calculated by the width and length of the membrane. In yet another example, at least a quarter, a third, half or all reagent dots have a diameter or surface area that is about 10%, 5%, 1%, 0.5%, 0.1%, 0.05%, 0.01%, 0.001% or smaller diameter or surface area of the length, width or surface of the matrix.

Any suitable drop volumes can be used to make spots with any suitable or desirable sizes. In exemplary embodiments, the range of drop volumes used to create the range of spot sizes on the flow membrane can be in the range of about 30-200 pL, 201-500 pL, 501 pL-1.001 mL, 1.001 mL to 5.0 mL, 5.1-25 mL, 21.1-100 mL, or 100.1-500 mL. Shown in the below Table 1 is both spherical and hemispherical diameter of various drop sizes in the above drop range.

TABLE 1

| Drop Volume | Sphere Diameter (um) | Hemisphere Size (um) |
|---|---|---|
| 1 pL | 12.4 | 15.3 |
| 10 | 26.7 | 33.8 |
| 100 | 58 | 72 |
| 500 | 98 | 124 |
| 1 nL | 124 | 156 |
| 2.08 | 158 | 199 |
| 5 | 212 | 268 |
| 10 | 266 | 337 |
| 20 | 336 | 423 |
| 50 | 457 | 577 |
| 100 | 575 | 725 |
| 500 | 982 | 1243 |

The actual developed spot size of a reagent drop on the membrane can be larger, e.g., about 10-25% larger, than the hemispherical drop diameter. The sphere and hemispherical size of different drop volumes with the range described above is shown in the above Table 1.

The meaning of a "diameter" is often determined by the shape of the dot. For example, if the dot is a circle, the diameter of a circle is any straight line segment that passes through the center of the circle and whose endpoints are on the circle. The length of a diameter is also called the diameter. For a convex shape in the plane, the diameter is defined to be the largest distance that can be formed between two opposite parallel lines tangent to its boundary. The use of "diameter" does not limit the dot shape to be a circle or other regular shape. In some specific embodiments, when a dot has an irregular shape, a "diameter" can be measured as a parameter that indicates the length or width of the dot, e.g., measured as the largest distance between two points on the dot.

The reagent dots in the test device can have the same or different size(s) or diameter(s). In one example, at least a quarter, a third, half or all reagent dots have substantially the same size or diameter. In another example, at least a quarter, a third, half or all reagent dots have substantially different sizes or diameters.

The reagent dots in the test device can have any suitable shapes, e.g., any suitable regular or irregular shape. In one example, at least one of the reagent dots has a shape that is a line, a circle, a rod, a square, a triangle, a rectangle or an irregular shape. In another example, at least a quarter, a third, half or all reagent dots have a shape that is a line, a circle, a rod, a square, a triangle, a rectangle or an irregular shape. The reagent dots in the test device can have the same or different shape(s). In one example, at least a quarter, a third, half or all reagent dots have the same shape. In another example, at least a quarter, a third, half or all reagent dots have different shapes.

The reagent dots can have any suitable space(s) or distance(s) between or among the dots. In one example, the distance between or among the reagent dots is about 1-10 um, 10-50 um, 51-100 um, 101-200 um, 201-300 um, 301-400, 401-500, or 501-600 um. The space(s) or distance(s) between or among the reagent dots can be the same or different. In one example, the space or distance between at least a quarter, a third, half or all reagent dots is substantially the same. In another example, the space or distances between at least a quarter, a third, half or all reagent dots are different. Such space or distance can be measured by any suitable means. In some specific embodiments, the space or distance between or among reagent dots is measured as the space or distance between or among the edges of the reagent dots or adjacent reagent dots, e.g., distance between or among the edges of dots which defines the low resistance flow path of reagents. In other specific embodiments, the space or distance between or among reagent dots is measured as the space or distance between or among the centers or effective centers of the reagent dots or adjacent reagent dots.

The reagent dots can be located on any suitable places or side(s) of the matrix. In one example, the test device comprises a single layer of the plurality of reagent dot. In another example, the test device comprises multiple layers, e.g., 2, 3, 4, 5, 6, 7, 8, 9, 10 or more layers, of the plurality of reagent dots. In still another example, the test device comprises at least a layer of the plurality of reagent dots on one side of the matrix. In yet another example, the test device comprises at least a layer of the plurality of reagent dots on both sides of the matrix.

The signal(s) at the reagent dots can be generated by any suitable reactions, such as chemical, biochemical, electrochemical, and/or binding reactions involving the analyte, the reagents located at the reagent dots, reagents added to the liquid sample and/or other liquid(s), and/or other reagents dried on the test device before use and that are transported by the liquid sample or other liquids to the reagent dots.

In some embodiments, the signal(s) at the reagent dots are generated based on binding reactions involving the analyte, the reagents located at the reagent dots, reagents added to the liquid sample and/or other liquid(s), and/or other reagents dried on the test device before use and that are transported by the liquid sample or other liquids to the reagent dots. In one example, at least one of the reagent dots comprises a reagent that is capable of binding to an analyte or another binding reagent that is capable of binding to an analyte. Preferably, the reagent is capable of specifically binding to an analyte or another binding reagent that is capable of binding to an analyte. Also preferably, the reagent avoids binding to interfering moiety or moieties in the testing sample. In another example, at least a quarter, a third, half or all reagent dots comprise a reagent that is capable of binding to an analyte or another binding reagent that is capable of binding to an analyte. Preferably, the reagents are capable of specifically binding to an analyte or another binding reagent that is capable of binding to an analyte.

The reagents located at the reagent dots can be any suitable substances. For example, the reagents can be inorganic molecules, organic molecules or complexes thereof. Exemplary inorganic molecules can be ions such as sodium, potassium, magnesium, calcium, chlorine, iron, copper, zinc, manganese, cobalt, iodine, molybdenum, vanadium, nickel, chromium, fluorine, silicon, tin, boron or arsenic ions. Exemplary organic molecules can be an amino acid, a peptide, a protein, e.g., an antibody or receptor, a nucleoside, a nucleotide, an oligonucleotide, a nucleic acid, e.g., DNA or RNA, a vitamin, a monosaccharide, an oligosaccharide, a carbohydrate, a lipid and a complex thereof.

Exemplary amino acids can be a D- or a L-amino-acid. Exemplary amino acids can also be any building blocks of naturally occurring peptides and proteins including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V).

Any suitable proteins or peptides can be used as the reagents on the test device. For example, enzymes, transport proteins such as ion channels and pumps, nutrient or storage proteins, contractile or motile proteins such as actins and myosins, structural proteins, defense protein or regulatory proteins such as antibodies, hormones and growth factors can be used. Proteineous or peptidic antigens can also be used.

Any suitable nucleic acids, including single-, double and triple-stranded nucleic acids, can be used as the reagents on the test device. Examples of such nucleic acids include DNA, such as A-, B- or Z-form DNA, and RNA such as mRNA, tRNA and rRNA.

Any suitable nucleosides can be can be used as the reagents on the test device. Examples of such nucleosides include adenosine, guanosine, cytidine, thymidine and uridine. Any nucleotides can be used as the reagents on the test device. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

Any suitable vitamins can be used as the reagents on the test device. For example, water-soluble vitamins such as thiamine, riboflavin, nicotinic acid, pantothenic acid, pyridoxine, biotin, folate, vitamin $B_{12}$ and ascorbic acid can be used. Similarly, fat-soluble vitamins such as vitamin A, vitamin D, vitamin E, and vitamin K can be used.

Any suitable monosaccharides, whether D- or L-monosaccharides and whether aldoses or ketoses, can be used as the reagents on the test device. Examples of monosaccharides include triose such as glyceraldehyde, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Any suitable lipids can be used as the reagents on the test device. Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

In one specific embodiment, the analyte to be detected comprises or is an antigen, the binding reagent on the test device comprises or is an antibody. Preferably, the antibody specifically binds to the analyte. In one example, the test device is used in a sandwich assay format, in which a binding reagent, e.g., an antibody, is used as a reagent at the reagent dots, and another binding reagent having a detectable label is also used to form a labeled binding reagent-analyte-binding reagent or antibody sandwich at the reagent dots to generate readout signals. Alternatively, a binding reagent is used as a reagent at the reagent dots, and an antibody have a detectable label is also used to form a labeled antibody-analyte-binding reagent sandwich at the reagent dots to generate readout signals. In one example, the sandwich assay uses two antibodies, one as the capture reagent and the other as the labeled reagent.

The test device can also used in a competition assay format. In one example, a binding reagent, e.g., an antibody, is used as a capture reagent at the reagent dots. An analyte or analyte analog having a detectable label, either added in a liquid or previously dried on the test device and redissolved or resuspnded by a liquid, will compete with an analyte in a sample to bind to the capture reagent at the reagent dots. In another example, an analyte or analyte analog is used as a capture reagent at the reagent dots. A binding reagent, e.g., an antibody, having a detectable label, is either added in a liquid or previously dried on the test device and redissolved or resuspnded by a liquid. An analyte in a sample will compete with the analyte or analyte analog at the reagent dots for binding to the binding reagent, e.g., an antibody, having a detectable label.

The matrix can have any suitable structure. In one example, the matrix can have a porous structure. The matrix can comprise any suitable material(s). For example, porous plastics material, such as polypropylene, polyethylene (preferably of very high molecular weight), polyvinylidene flouride, ethylene vinylacetate, acrylonitrile and polytetrafluoroethylene can be used. See e.g., U.S. Pat. No. 6,187,598. It can be advantageous to pre-treat the member with a surface-active agent during manufacture, as this can reduce any inherent hydrophobicity in the member and therefore enhance its ability to take up and deliver a moist sample rapidly and efficiently. The matrix can also be made from paper or other cellulosic materials. In some embodiments, the matrix comprises or is made of nitrocellulose or glass fiber.

In another example, the matrix can have a non-porous structure, e.g., plastic solid surface. In some embodiments, the matrix can have other structures such as channels or other guided fluid pathways. In another example, the matrix comprises a plastic, a film of a matrix having a hydrophilic surface, or a material with a controlled contact angle with the sample liquid.

The reagent dots can comprise any suitable reagents and can be arranged to form any suitable pattern. In one example, the plurality of reagent dots comprises the same binding reagent that is capable of binding to an analyte or another binding reagent that is capable of binding to the analyte. The plurality of reagent dots form a line that is substantially parallel to the liquid sample flow direction. As the liquid sample flows laterally along the test device, the analyte, if present in the liquid sample, becomes sequentially bound to the binding reagent at each of the reagent dots until the analyte is depleted by binding to the upstream reagent dot(s). The binding of the analyte to the reagent dot(s) generates a dateable signal at the reagent dot(s), and the intensity and/or the number of the dateable signal at the reagent dot(s) provides a quantitation or a semi-quantitation of the analyte in the liquid sample.

In another example, the plurality of reagent dots comprises different binding reagents that are capable of binding to different analytes or other binding reagents that are capable of binding to the analytes. The plurality of reagent dots forms a line that is substantially parallel to the liquid sample flow direction. As the liquid sample flows laterally along the test device, the analytes, if present in the liquid sample, become bound to the binding reagents at each of the reagent dots. The binding of the analytes to the reagent dots generates dateable signals at the reagent dots, and the presence and/or intensity of the dateable signals at the reagent dots indicates the presence and/or amount of the analytes in the liquid sample.

In still another example, the plurality of reagent dots comprises different groups of binding reagents, each group of the binding reagents is capable of binding to the same analyte or another binding reagent that is capable of binding to the same analyte, and the binding reagents in different groups are capable of binding to different analytes or other binding reagents that are capable of binding to different analytes. Each group of the reagent dots forms a line that is substantially parallel to the liquid sample flow direction, and the different lines formed by the different groups of the reagent dots are substantially parallel to each other. As the liquid sample flows laterally alone the test device, the analytes, if present in the liquid sample, become sequentially bound to the binding reagents at each of the reagent dots in each group of the reagent dots until the analytes are depleted by binding to the upstream reagent dots. The binding of the analytes to the reagent dots generates dateable signals at the reagent dots, and the intensity and/or the number of the dateable signals at the reagent dots provides a quantitation or a semi-quantitation of the different analytes in the liquid sample.

In yet another example, the plurality of reagent dots comprises the same binding reagent that is capable of binding to an analyte or another binding reagent that is capable of binding to the analyte. The plurality of reagent dots forms multiple lines that are substantially parallel to the liquid sample flow direction. The reagent dots in each line comprise the same amount of the binding reagent, but the reagent dots in different lines comprise the different amounts of the binding reagent. As the liquid sample flows laterally alone the test device, the analyte, if present in the liquid sample, becomes sequentially bound to the binding reagent at each of the reagent dots in each of the lines until the analyte is depleted by binding to the upstream reagent dot(s) in each of the lines. The binding of the analyte to the reagent dot(s) generates a dateable signal at the reagent dot(s), and the intensity and/or the number of the dateable signal at the reagent dot(s) provides a quantitation or a semi-quantitation of the analyte in the liquid sample. The reagent dots in different lines can comprise the same or different amounts of the binding reagent. In one embodiment, from one end to the other end of the test device, in the direction perpendicular to the direction of said liquid sample flow, the reagent dots in different lines comprise the sequentially different amounts of the binding reagent, e.g., sequentially increasing or decreasing amounts of the binding reagent.

In yet another example, the plurality of reagent dots comprises two different groups of binding reagents. One group of the reagent dots forms a line that is at a first angle relative to the liquid sample flow direction, and the other group of the reagent dots forms a line that is at a second, different angle relative to the liquid sample flow direction. After the liquid sample flows laterally along the test device, the reagent dots in one of the lines generate a signal indicating the presence and/or amount of an analyte in the liquid sample, and the reagent dots in the other line generate a control signal indicating the test is properly conducted. When the liquid sample comprises the analyte and the test is properly conducted, the two lines of the reagent dots generate a positive symbol, indicating the presence and/or amount of the analyte in the liquid sample. When the liquid sample does not comprise the analyte and the test is properly conducted, only one line of the reagent dots generates a negative symbol, indicating the absence of the analyte in the liquid sample.

The two different groups of binding reagents can form lines that are at any suitable angles relative to the liquid sample flow direction, and the reagent dots can form any suitable readout signals to indicate the presence, absence and/or amount of the analyte in the liquid sample. For example, one group of the reagent dots forms a line that is substantially parallel to the liquid sample flow direction, and the other group of the reagent dots forms a line that is substantially perpendicular to the liquid sample flow direction. When the liquid sample comprises the analyte and the test is properly conducted, the two lines of the reagent dots generate a "+" symbol, indicating the presence and/or amount of the analyte in the liquid sample, and when the liquid sample does not comprise the analyte and the test is properly conducted, only one line of the reagent dots generates a "-" symbol, indicating the absence of the analyte in the liquid sample.

In yet another example, the plurality of reagent dots comprises two different groups of binding reagents. After the liquid sample flows laterally along the test device, reagent dots in one group generate an alpha-numeric signal indicating the presence and/or amount of an analyte in the liquid sample, and the reagent dots in the other group generate a control symbol signal indicating the test is properly conducted. The alpha-numeric signal can take any suitable forms. For example, the alpha-numeric signal can be a word such as yes, Pos, Positive, Neg, Negative, No, or OK. The control symbol signal can also take any suitable forms. For example, the control symbol signal can be a "+" sign. The test device can be configured for any suitable form of test, e.g., a sandwich or competitive test.

In yet another example, the test device can comprise at least one group of the reagent dots that generate an additional signal that is not related to the presence, absence and/or amount of the analyte in the liquid sample, or whether the test is properly conducted. Such additional reagent dots can be used for any suitable purposes. For example, the additional signal can be used to indicate the authenticity, quality and/or identification of the test device, or identification of the liquid sample. The additional signal can have any suitable form or pattern. For example, the additional signal can comprise an alpha-numeric signal.

In yet another example, the test device can comprise at least one group of the reagent dots that form a circle around the sample application location, and the liquid sample moves radially to pass the group of the reagent dots. In yet another example, the test device can further comprise a flow through device portion.

The matrix can have any suitable form or shape. For example, the matrix can be in the form of a strip or a circle. The matrix can also have suitable number of elements. For example, the matrix can be made of a single element or can comprise multiple elements.

The test device can further comprise a sample application element upstream from and in fluid communication with the matrix. The sample application element can be made of any suitable materials, such as nitrocellulose, glass fiber, polypropylene, polyethylene (preferably of very high molecular weight), polyvinylidene flouride, ethylene vinylacetate, acrylonitrile or polytetrafluoro-ethylene. The matrix and the sample application element can comprise the same or different materials.

The test device can further comprise a liquid absorption element downstream from and in fluid communication with the matrix. The liquid absorption element can be made of any suitable materials, such as paper or cellulose materials.

The test device can further comprise a control location comprising means for indicating proper flow of the liquid sample and/or a valid test result. Any suitable means can be used. In one example, the means comprises a binding reagent that binds to a binding reagent with a detectable label that also binds to the analyte. In another example, the means comprises a binding reagent that binds to a binding reagent with a detectable label that does not bind to the analyte. In still another example, the means comprises a substance that will generate a detectable signal, e.g., color or electrical signal, once a liquid flow along or through the control location.

In some embodiments, at least a portion of the matrix is supported by a solid backing. In other embodiments, half, more than half or all portion of the matrix is supported by a solid backing. The solid backing can be made of any suitable material, e.g., solid plastics. If the test device comprises electrode or other electrical elements, the solid backing should generally comprise non-conductive materials.

In some embodiments, a labeled reagent can be dried on the test device and the dried labeled reagent can be redissolved or resuspended by a liquid, e.g., a sample liquid and/or additional liquid, and transported laterally through the test device to generate readout, control and/or other signals. For example, a portion of the matrix, upstream from the at least two of the reagent dots, can comprise a dried, labeled reagent, the labeled reagent capable of being moved by a liquid sample and/or a further liquid to the at least two of the reagent dots and/or a control location to generate a detectable signal. The dried, labeled reagent can be located at any suitable places on the test device. In one example, the dried, labeled reagent is located downstream from a sample application place on the test device. In another example, the dried, labeled reagent is located upstream from a sample application place on the test device. The type of the labeled reagent can be determined based on the intended assay formats. For example, if the test device is to be used in a sandwich assay, the labeled reagent should be capable of binding, and preferably capable of specifically binding, to the analyte or another substance that binds to the analyte. The same labeled reagent can also be used for certain competitive binding assays. For other types of the competitive binding assays, the labeled reagent should be an analyte or an analyte analog linked to a detectable label.

In some embodiments, the test device can further comprise, upstream from the at least two of the reagent dots, a conjugate element that comprises a dried, labeled reagent, the labeled reagent being capable of moved by a liquid sample and/or a further liquid to the at least two of the reagent dots and/or a control location to generate a detectable signal. The conjugate element can be located downstream from a sample application place on the test device. The conjugate element can also be located upstream from a sample application place on the test device. In some embodiments, the labeled reagent binds to an analyte in the liquid sample. In other embodiments, the labeled reagent competes with an analyte in the liquid sample for binding to a binding reagent for the analyte at the at least two of the reagent dots.

Any suitable label can be used. The label can be a soluble label, such as a colorimetric, radioactive, enzymatic, luminescent or fluorescent label. The label can also be a particle or particulate label, such as a particulate direct label, or a colored particle label. Exemplary particle or particulate labels include colloidal gold label, latex particle label, nanoparticle label and quantum dot label. Depending on the specific configurations, the labels such as colorimetric, radioactive, enzymatic, luminescent or fluorescent label, can be either a soluble label or a particle or particulate label.

In some embodiments, the labeled reagent is dried in the presence of a material that stabilizes the labeled reagent, facilitates solubilization or resuspension of the labeled reagent in a liquid, and/or facilitates mobility of the labeled reagent. Any suitable material can be used. For example, the material can be a protein, e.g., a meta-soluble protein, a peptide, a polysaccharide, a sugar, e.g., sucrose, a polymer, a gelatin or a detergent. See e.g., U.S. Pat. Nos. 5,120,643 and 6,187,598.

The present test devices can be used with any suitable sample liquid. In one example, a sample liquid alone is used to transport the analyte and/or the labeled reagent to the at least two of the reagent dots. In another example, a developing liquid is used to transport the analyte and/or the labeled reagent to the at least two of the reagent dots. In still another example, both sample liquid and a developing liquid is used to transport the analyte and/or the labeled reagent to the at least two of the reagent dots.

In some embodiments, the test device can further comprise a housing that covers at least a portion of the test device, wherein the housing comprises a sample application port to allow sample application upstream from or to the at least two of the reagent dots and an optic opening around the at least two of the reagent dots to allow signal detection at the two of the reagent dots. The optic opening can be achieved in any suitable way. For example, the optic opening can simply be an open space. Alternatively, the optic opening can be a transparent cover.

In other embodiments, the housing can cover the entire test device. In still other embodiments, at least a portion of the sample receiving portion of the matrix or the sample application element is not covered by the housing and a sample is applied to the portion of the sample receiving portion of the matrix or the sample application element outside the housing and then transported to the at least two of the reagent dots. The housing can comprise any suitable material. For example, the housing can comprise a plastic material, a biodegradable material or a cellulosic material. In another example, the housing, whether in part or in its entirety, can comprise an opaque, translucent and/or transparent material.

In some embodiments, the present invention provides for a test device wherein the liquid sample has moved laterally along the test device to generate detectable signal(s) at the at least two of the reagent dots.

C. Methods for Detecting an Analyte Using a Lateral Flow Device with Two Dimensional Features In still another aspect, the present disclosure provides for a method for detecting an analyte in a liquid sample, which method comprises: a) contacting a liquid sample with any of the test devices described in the above Section V.B., wherein the liquid sample is applied to a site of the test device upstream of the plurality of reagent dots; b) transporting an analyte, if present in the liquid sample, and a labeled reagent to the plurality of reagent dots; and c) assessing the presence, absence, amount and/or pattern of signal(s) generated by the labeled reagent at the plurality of reagent dots to determining the presence, absence and/or amount of the analyte in the liquid sample.

In another exemplary embodiment, the signal(s) at the reagent dots can be generated by binding reactions involving the analyte and the reagents located at the reagent dots, and a labeled reagent added to the liquid sample or dried on the test device before use and is transported by the liquid sample or other liquids to the reagent dots. For example, the method comprises a) contacting a liquid sample with the above test device, wherein the liquid sample is applied to a site of the test device upstream of the at least two of the reagent dots; b) transporting an analyte, if present in the liquid sample, and a labeled reagent to the at least two of the reagent dots; and c) assessing the presence, absence, amount and/or pattern of signal(s) at the at least two of the reagent dots, e.g., signal(s) generated by the labeled reagent at the at least two of the reagent dots, to determining the presence, absence and/or amount of the analyte in the liquid sample.

In some embodiments, the liquid sample and the labeled reagent are premixed to form a mixture and the mixture is applied to the test device. For example, the labeled reagent can be provided or stored in a liquid and then can be premixed with a sample liquid to form a mixture and the mixture is applied to the test device. In another example, the labeled reagent can be dried in a location or container not in fluid communication with the test device, e.g., in a test tube or well such as a microtiter plate well. In use, the sample liquid can be added to the container, e.g., the test tube or well, to form the mixture and the mixture can then be applied to the test device.

In other embodiments, the test device comprises a dried labeled reagent before use and the dried labeled reagent is solubilized or resuspended, and transported to the at least two of the reagent dots by the liquid sample and/or other liquid. The dried labeled reagent can be located at any suitable location on the test device. For example, the dried labeled reagent can be located downstream from the sample application site, and the dried labeled reagent can be solubilized or resuspended, and transported to the at least two of the reagent dots by the liquid sample and/or other liquid. In another example, the dried labeled reagent can be located upstream from the sample application site, and the dried labeled reagent can be solubilized or resuspended, and transported to the at least two of the reagent dots by another liquid.

In some embodiments, the labeled reagent is solubilized or resuspended, and transported to the at least two of the reagent dots by the liquid sample alone. In other embodiments, the analyte and/or labeled reagent is solubilized or resuspended, and transported to the at least two of the reagent dots by another liquid. In still other embodiments, the analyte and/or labeled reagent is solubilized or resuspended, and transported to the at least two of the reagent dots by both the sample liquid and another liquid, e.g., a developing liquid.

The present test devices can be used to detect an analyte in any suitable sample liquid. In some embodiments, the liquid sample can be body fluid sample, such as a whole blood, a serum, a plasma, a urine sample or an oral fluid. Such body fluid sample can be sued directly or can be processed, e.g., enriched, purified, or diluted, before use. In other embodiments, the liquid sample can be a liquid extract, suspension or solution derived from a solid or semi-solid biological material such as a phage, a virus, a bacterial cell, an eukaryotic cell, a fugal cell, a mammalian cell, a cultured cell, a cellular or subcellular structure, cell aggregates, tissue or organs. In specific embodiments, the sample liquid is obtained or derived from a mammalian or human source. In still other embodiments, the liquid sample is a sample derived from a biological, a forensics, a food, a biowarfare, or an environmental source. In other embodiments, the sample liquid is a clinical sample, e.g., a human or animal clinical sample. In still other embodiments, the sample liquid is a man-made sample, e.g., a standard sample for quality control or calibration purposes.

The present test devices can be used to detect the presence, absence and/or amount of an analyte in any suitable sample liquid. In some embodiments, the present test devices are used to detect the presence or absence of an analyte in any suitable sample liquid, i.e., to provide a yes or no answer. In other embodiments, the present test devices are used to quantify or semi-quantify the amount of an analyte in a liquid sample.

The present test devices can be used to detect the presence, absence and/or amount of a single analyte in any suitable sample liquid. Alternatively, the present test devices can be used to detect the presence, absence and/or amount of multiple analytes in a liquid sample. In still other embodiments, the present test devices can be used to quantify or semi-quantify the amounts of the multiple analytes in the liquid sample.

The present test devices can be used to detect the presence, absence and/or amount of any suitable analyte in a sample liquid. Exemplary analytes include inorganic molecules, organic molecules or complexes thereof. Exemplary inorganic molecules can be ions such as sodium, potassium, magnesium, calcium, chlorine, iron, copper, zinc, manganese, cobalt, iodine, molybdenum, vanadium, nickel, chromium, fluorine, silicon, tin, boron or arsenic ions. Exemplary organic molecules can be an amino acid, a peptide, a protein, a nucleoside, a nucleotide, an oligonucleotide, a nucleic acid, e.g., a DNA or RNA molecule or a hybrid thereof, a vitamin, a monosaccharide, an oligosaccharide, a carbohydrate, a lipid and a complex thereof. In some embodiments, the analyte is a cell, a virus or a molecule. In other embodiments, the analyte is hCG, hLH, hFSH, hTSH, a disease or disorder marker, e.g., a cardiac biomarker, an antigen of an infectious organism, an antibody to an infectious organism, etc.

The present methods can be used for any suitable purpose. For example, present methods can be used for clinical diagnosis, prognosis, risk assessment and prediction, stratification and treatment monitoring and adjustment. In another example, present methods can be used for various research purposes, such as basic research, drug candidate screening, animal studies, and clinical trials. In still another example, present methods can be used in tests for standard setting, quality control, illegal drug screening, food safety, environmental safety, industrial safety, pollution, detection of biowarfare agents, screening for drugs or pharmaceuticals, and monitoring the quality of manufacturing using bioreactors looking for unwanted molecules, etc. The present tests devices and methods can be used in any suitable settings, such as tests in the labs, clinics, hospitals, physician's offices, homes, natural environments, battle fields and first responder environments, e.g., environments for fire, paramedic, police actions.

D. Exemplary Embodiments

Attempts were made previously to generate a binary result in a lateral flow assay using symbols rather than lines. For example, in a sandwich assay, the presence of a "Test Line" can be used to indicate the presence of the analyte of interest. A second, feature, a "Control Line" can be generated whether the analyte is present or absent. Thus, no matter whether the test is positive or negative, the Control Line feature is always formed.

In certain "Digital" lateral flow assays, where the formation of test and control lines (or sometimes just test lines) is evaluated by a digital reader system, the result is reported to the user as an intuitive set of symbols—digitally generated—that form words such as "Positive"—if the test line is present—or "Negative" where the test line is not present. This result, as far as the user is concerned, is a binary one. Either the word Positive or the word Negative is generated by the onboard computer. Both sets of symbols do not appear together.

One embodiment of the Symbolics technology is the generation of test and control features that are not just lines. Rather, they can be easily interpreted combinations of alpha-numeric symbols. As a result, Symbolics technology based lateral flow assays can generate easily interpreted signals such as the words "positive" or "negative." These symbols are created by the generation of the actual test result, not by a digital reporting system that has interpreted the presence or absence of a test line and generated the word "positive" or "negative" on a screen for the user to read.

In some embodiments, the concept of "binary" reporting in the context of Symbolics technology carries a challenge with it. In some embodiments, Symbolics technology does not generate a test line that is interpreted by a digital reader and is transduced by software or firmware into another set of symbols for interpretation by the user. Instead, it uses the capture reagents for the assay, printed in the form of the symbols or words, to directly generate a set of results for an assay, that are directly interpreted by the user. To understand the challenge, an understanding of the principle of test and control feature formation is needed.

In some embodiments, in order for a Test feature (a "Positive") to appear in a sandwich assay, the analyte must create a bridge between the capture reagent, which has been printed in the form of a line, or—for argument's sake—as the word "Positive" in the reaction matrix. It must also in turn capture a reactive conjugate as it flows past the symbols, in order to create the visible line or the word "Positive"

for the reader to interpret. If the analyte is not present, that line or word will not form and the conjugate will flow to the control region, where the control capture reagents will directly capture the reactive conjugate and generate a second line or set of symbols, printed for example in the shape of the word "Negative".

Accordingly, in some embodiments, due to the method by which the control works, the control feature will form whether or not the analyte is present, as the purpose of the control is to indicate that the test has run properly and/or the right type of sample has been used. As a result, in some embodiments, in the absence of the analyte, the Test symbols ("Positive") will not form and the Control symbols will form the word "Negative", so the user sees only the word "Negative" and interprets the assay as being negative. However, in the presence of analyte, the Test symbols will form the word "Positive" and the control symbols will still form the word "Negative" so both sets of features will form. This may not be an acceptable embodiment, as it will be confusing to a user.

Figure 2:
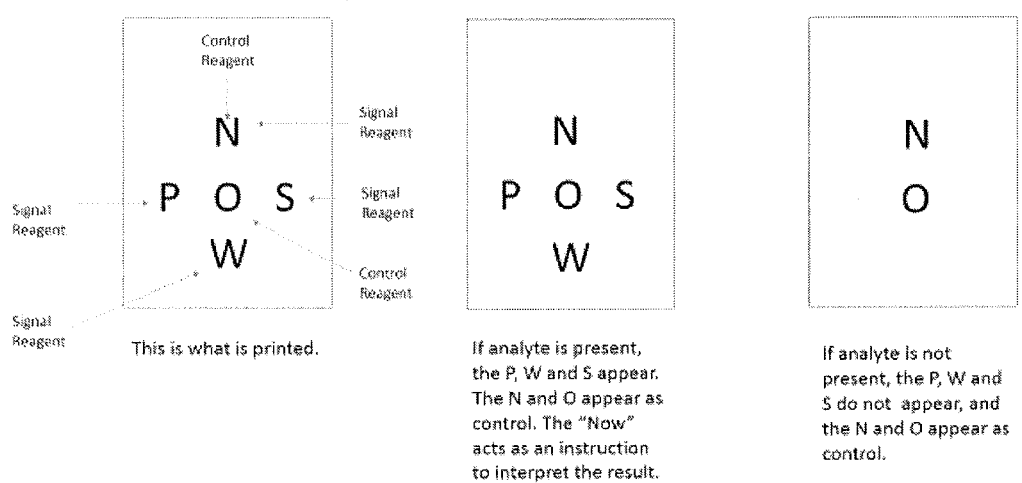
FIG. 2 illustrates another exemplary lateral flow test format using two dimensional test and control signal readout patterns.

Therefore, in some embodiments, an alternative way of intuitively signaling the presence of the analyte must be generated that is not confusing to the user. Two exemplary embodiments are illustrated in FIGS. 1 and 2 and described below that are designed to address the issue of "binary" result formation in Symbolics technology based lateral flow tests. FIGS. 1 and 2 illustrative two potential printing patterns for test and control reagents in lateral flow assays that can generate intuitive, and effectively binary results for users. In other words, different intuitive result readouts can be generated in the presence and absence of the analyte. These are just examples, intended for English language users. Other similar embodiments are contemplated, e.g., suitable to be used in other languages.

FIG. 1 illustrates an exemplary lateral flow test format using two dimensional test and control signal readout patterns. The sample flow direction is from bottom to top. After a liquid sample containing no analyte or an analyte below detection level flows laterally along the test device and passes a plurality of reagent dots, a combination of two dimensional features, viewed from a direction substantially opposite to the liquid sample flow direction, forms the word "NO," indicating a valid, negative test result. After a liquid sample containing an analyte at or above detection level flows laterally along the test device and passes a plurality of reagent dots, additional signal feature obscures the above letter "N," and a combination of additional signal features and the above letter "O", viewed from a direction substantially perpendicular to the liquid sample flow direction, forms the phrase "POS," indicating a valid, positive test result. The matrix of the test device comprises, at the locations for generating letters "N" and "O," a control reagent. The matrix of the test device comprises, at the locations for generating letters "P," "S" and the area covering the letter "N" (excluding the area for generating the letter N itself), a test reagent.

FIG. 2 illustrates another exemplary lateral flow test format using two dimensional test and control signal readout patterns. The sample flow direction is from bottom to top. After a liquid sample containing no analyte or an analyte below detection level flows laterally along the test device and passes a plurality of reagent dots, a combination of two dimensional features, viewed from a direction substantially opposite to the liquid sample flow direction, forms the word "NO," indicating a valid, negative test result. After a liquid sample containing an analyte at or above detection level flows laterally along the test device and passes a plurality of reagent dots, a combination of additional signal features and the above letter "O", viewed from a direction substantially perpendicular to the liquid sample flow direction, forms the phrase "POS," indicating a valid, positive test result, and a combination of an additional signal feature and the above letters "N" and "O," viewed from a direction substantially opposite to the liquid sample flow direction, forms the word "NOW," which can be used to aid interpretation of the test result. The matrix of the test device comprises, at the locations for generating letters "N" and "0," a control reagent. The matrix of the test device comprises, at the locations for generating letters "P," "S" and "W," a test reagent.

The present invention is further illustrated by the following exemplary embodiments:

1. A test device for detecting an analyte in a liquid sample, which device comprises a plurality of reagent dots on a matrix, wherein at least two of said reagent dots do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, and:
   1) after a liquid sample containing no analyte or an analyte below detection level flows laterally along said test device and passes said plurality of reagent dots, said plurality of reagent dots form two separate two-dimensional signal features A and B, and said feature A, feature B or a combination thereof, viewed from a direction substantially parallel or opposite to the liquid sample flow direction, indicates that a test is properly conducted and said sample contains no analyte or the analyte below detection level; or
   2) after a liquid sample containing an analyte at or above detection level flows laterally along said test device and passes said plurality of reagent dots, said plurality of reagent dots:
      a) form one discernible feature that is one of said features A and B, form additional signal feature C that obscures the other of said features A and B to form an obscured feature D, and said discernible feature from features A and B or a combination of said discernible feature from features A and B and said obscured feature D, viewed from a direction substantially parallel or opposite to the liquid sample flow direction, indicates that a test is properly conducted; and
      b) form at least one additional two-dimensional signal feature E, and a combination of said discernible feature from features A and B and said feature E, viewed from a direction substantially perpendicular to the liquid sample flow direction, indicates that said sample contains said analyte at or above detection level.

2. The test device of embodiment 1, wherein the plurality of reagent dots form at least two additional two-dimensional signal features E and E', and a combination of the discernible feature from features A and B and the features E and E', viewed from a direction substantially perpendicular to the liquid sample flow direction, indicates that the sample contains the analyte at or above detection level.

3. The test device of embodiment 1 or 2, wherein at least one, some or all of the features A-E', or a combination thereof, comprises a predetermined pattern that is selected from the group consisting of a line, multiple lines, a symbol, a geometric shape and an alpha-numeric shape.

4. The test device of embodiment 3, wherein the alpha-numeric shape is a letter, a word, a number or a combination thereof.

5. The test device of embodiment 4, wherein the combination of the features A and B, viewed from a direction substantially parallel or opposite to the liquid sample flow direction, forms the word "NO."

6. The test device of embodiment 4, wherein the combination of the discernible feature from features A and B and the features E and E', viewed from a direction substantially perpendicular to the liquid sample flow direction, forms the phrase "POS."

7. The test device of embodiment 3, wherein the obscured feature D is a geometric shape.

8. The test device of any of the embodiments 1-7, wherein the matrix comprises, at the locations for generating features A and/or B, a control reagent.

9. The test device of embodiment 8, wherein the control reagent comprises a binding reagent that is capable of binding to a non-analyte substance in the sample and/or a test reagent.

10. The test device of any of the embodiments 1-9, wherein the matrix comprises, at the locations for generating features C, E, and/or E and E', a test reagent.

11. The test device of embodiment 10, wherein the test reagent comprises a binding reagent that is capable of binding to an analyte or another binding reagent that is capable of binding to an analyte.

12. A test device for detecting an analyte in a liquid sample, which device comprises a plurality of reagent dots on a matrix, wherein at least two of said reagent dots do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, and:

1) after a liquid sample containing no analyte or an analyte below detection level flows laterally along said test device and passes said plurality of reagent dots, said plurality of reagent dots form two separate two-dimensional signal features A and B, said feature A, feature B or a combination thereof, viewed from a direction substantially parallel or opposite to the liquid sample flow direction, indicates that a test is properly conducted and said sample contains no analyte or the analyte below detection level; or 2) after a liquid sample containing an analyte at or above detection level flows laterally along said test device and passes said plurality of reagent dots, said plurality of reagent dots:

a) form two separate two-dimensional signal features A and B and an additional signal feature C, said feature A, feature B or a combination thereof, viewed from a direction substantially parallel or opposite to the liquid sample flow direction, indicates that a test is properly conducted, and a combination of one or both of said features A and B and said feature C, viewed from a direction substantially parallel or opposite to the liquid sample flow direction, generates a signal that aids interpretation of the test result; and b) form at least one additional two-dimensional signal feature E, and a combination of at least one of said features A and B and said feature E, viewed from a direction substantially perpendicular to the liquid sample flow direction, indicates that said sample contains said analyte at or above detection level.

13. The test device of embodiment 12, wherein the plurality of reagent dots form at least two additional two-dimensional signal features E and E', and a combination of one of the features A and B and the features E and E', viewed from a direction substantially perpendicular to the liquid sample flow direction, indicates that the sample contains the analyte at or above detection level.

14. The test device of embodiment 12 or 13, wherein at least one, some or all of the features A-E', or a combination thereof, comprises a predetermined pattern that is selected from the group consisting of a line, multiple lines, a symbol, a geometric shape and an alpha-numeric shape.

15. The test device of embodiment 14, wherein the alpha-numeric shape is a letter, a word, a number or a combination thereof.

16. The test device of embodiment 15, wherein the combination of the features A and B, viewed from a direction substantially parallel or opposite to the liquid sample flow direction, forms the word "NO."

17. The test device of embodiment 15, wherein the combination of one of the features A and B and the features E and E', viewed from a direction substantially perpendicular to the liquid sample flow direction, forms the phrase "POS."

18. The test device of embodiment 15, wherein the combination of the features A, B and C forms the word "NOW."

19. The test device of any of the embodiments 12-18, wherein the matrix comprises, at the locations for generating features A and/or B, a control reagent.

20. The test device of embodiment 19, wherein the control reagent comprises a binding reagent that is capable of binding to a non-analyte substance in the sample and/or a test reagent.

21. The test device of any of the embodiments 12-20, wherein the matrix comprises, at the locations for generating features C, E, and/or E and E', a test reagent.

22. The test device of embodiment 21, wherein the test reagent comprises a binding reagent that is capable of binding to an analyte or another binding reagent that is capable of binding to an analyte.

23. The test device of any of the embodiments 1-22, wherein the plurality of reagent dots comprises at least 3, 4, 5, 6, 7, 8, 9, 10, 20, 30, 40, 50, 60, 70, 80, 90, 100, 500, 1,000, 5,000, 10,000 or more reagent dots.

24. The test device of any of the embodiments 1-23, wherein at least a quarter, a third, half or all reagent dots do not overlap and are sufficiently spaced apart from each other so that when the liquid sample flows laterally along the matrix, flow of the liquid sample to, through and/or around one of the reagent dots does not substantially affect flow of the liquid sample to, through and/or around the other reagent dots.

25. The test device of any of the embodiments 1-24, wherein at least one of the reagent dots has a diameter of about 0.1-1 um, 1-10 um, 10-50 um, 51-100 um, 101-200 um, 201-300 um, 301-400 um, 401-500 um and 501-1000 um, or at least one of the reagent dots has a diameter or surface area that is about 10%, 5%, 1%, 0.5%, 0.1%, 0.05%, 0.01%, 0.001% or smaller diameter or surface area of the length, width or surface area of the matrix.

26. The test device of embodiment 25, wherein at least a quarter, a third, half or all reagent dots have a diameter of about 0.1-1 um, 1-10 um, 10-50 um, 51-100 um, 101-200 um, 201-300 um, 301-400 um, 401-500 um or 501-1000 um, or at least a quarter, a third, half or all reagent dots have a diameter or surface area that is about 10%, 5%, 1%, 0.5%, 0.1%, 0.05%, 0.01%, 0.001% or smaller diameter or surface area of the length, width or surface of the matrix.

27. The test device of the embodiment 25, wherein at least a quarter, a third, half or all reagent dots have substantially the same size or diameter.

28. The test device of any of the embodiments 1-27, wherein the distance between edges of at least two of the reagent dots is about 1-10 um, 10-50 um, 51-100 um, 101-200 um, 201-300 um, 301-400, 401-500, or 501-600 um.

29. The test device of the embodiment 28, wherein the distance between at least a quarter, a third, half or all reagent dots is substantially the same.

30. A method for detecting an analyte in a liquid sample, which method comprises:
a) contacting a liquid sample with the test device of any of the embodiments 1-29, wherein the liquid sample is applied to a site of the test device upstream of the plurality of reagent dots;
b) transporting an analyte, if present in the liquid sample, and a labeled reagent to the plurality of reagent dots; and
c) assessing the presence, absence, amount and/or pattern of signal(s) generated by the labeled reagent at the plurality of reagent dots to determining the presence, absence and/or amount of the analyte in the liquid sample.

31. The method of embodiment 30, wherein the liquid sample and the labeled reagent are premixed to form a mixture and the mixture is applied to the test device.

32. The method of embodiment 30, wherein the test device comprises a dried labeled reagent before use and the dried labeled reagent is solubilized or resuspended, and transported to the plurality of reagent dots by the liquid sample.

33. The method of embodiment 32, wherein the dried labeled reagent is located downstream from the sample application site, and the dried labeled reagent is solubilized or resuspended, and transported to the plurality of reagent dots by the liquid sample.

34. The method of embodiment 32, wherein the dried labeled reagent is located upstream from the sample application site, and the dried labeled reagent is solubilized or resuspended, and transported to the plurality of reagent dots by another liquid.

35. The method of embodiment 32, wherein the labeled reagent is solubilized or resuspended, and transported to the plurality of reagent dots by the liquid sample alone.

36. The method of embodiment 32, wherein the analyte and/or labeled reagent is solubilized or resuspended, and transported to the plurality of reagent dots by another liquid.

37. The method of any of the embodiments 30-36, wherein the liquid sample is body fluid sample.

38. The method of embodiment 37, wherein the body fluid sample is selected from the group consisting of a whole blood, a serum, a plasma and a urine sample.

39. The method of any of the embodiments 30-38, wherein the liquid sample is a sample derived from a biological, a forensics, a food, a biowarfare, or an environmental source.

40. The method of any of the embodiments 30-39, which is used to assess the presence or absence of an analyte in a liquid sample.

41. The method of any of the embodiments 30-40, which is used to detect multiple analytes in a liquid sample.

The ordinarily skilled artisan can appreciate that the present invention can incorporate any number of the preferred features described above.

Further features and advantages of the present invention will become apparent to those of skill in the art in view of the detailed description of preferred embodiments which follows, when considered together with the attached drawings and claims.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

Citation of the above publications or documents is not intended as an admission that any of the foregoing is pertinent prior art, nor does it constitute any admission as to the contents or date of these publications or documents.

What is claimed is:

1. A test device for detecting an analyte in a liquid sample, which device comprises a plurality of reagent dots on a matrix, wherein at least two of said reagent dots do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, and:
1) after a liquid sample containing no analyte or an analyte below detection level flows laterally along said test device and passes said plurality of reagent dots, said plurality of reagent dots form two separate two-dimensional signal features A and B, and said feature A, feature B or a combination thereof, viewed from a direction substantially parallel or opposite to the liquid sample flow direction, indicates that a test is properly conducted and said sample contains no analyte or the analyte below detection level; or
2) after a liquid sample containing an analyte at or above detection level flows laterally along said test device and passes said plurality of reagent dots, said plurality of reagent dots:
a) form one discernible feature that is one of said features A and B, form additional signal feature C that obscures the other of said features A and B to form an obscured feature D, and said discernible feature from features A and B or a combination of said discernible feature from features A and B and said obscured feature D, viewed from a direction substantially parallel or opposite to the liquid sample flow direction, indicates that a test is properly conducted; and
b) form at least one additional two-dimensional signal feature E, and a combination of said discernible feature from features A and B and said feature E, viewed from a direction substantially perpendicular to the liquid sample flow direction, indicates that said sample contains said analyte at or above detection level.

2. The test device of claim 1, wherein the plurality of reagent dots form at least two additional two-dimensional signal features E and E', and a combination of the discernible feature from features A and B and the features E and E', viewed from a direction substantially perpendicular to the liquid sample flow direction, indicates that the sample contains the analyte at or above detection level.

3. The test device of claim 1, wherein at least one, some or all of the features A-E', or a combination thereof, comprises a predetermined pattern that is selected from the group consisting of a line, multiple lines, a symbol, a geometric shape and an alpha-numeric shape.

4. The test device of claim 3, wherein the alpha-numeric shape is a letter, a word, a number or a combination thereof.

5. The test device of claim 4, wherein the combination of the features A and B, viewed from a direction substantially parallel or opposite to the liquid sample flow direction, forms the word "NO".

6. The test device of claim 4, wherein the combination of the discernible feature from features A and B and the features E and E', viewed from a direction substantially perpendicular to the liquid sample flow direction, forms the phrase "POS".

7. The test device of claim 3, wherein the obscured feature D is a geometric shape.

8. The test device of claim 1, wherein the matrix comprises, at the locations for generating features A and/or B, a control reagent.

9. The test device of claim 1, wherein the matrix comprises, at the locations for generating features C, E, and/or E and E', a test reagent.

10. A test device for detecting an analyte in a liquid sample, which device comprises a plurality of reagent dots on a matrix, wherein at least two of said reagent dots do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, and:
   1) after a liquid sample containing no analyte or an analyte below detection level flows laterally along said test device and passes said plurality of reagent dots, said plurality of reagent dots form two separate two-dimensional signal features A and B, said feature A, feature B or a combination thereof, viewed from a direction substantially parallel or opposite to the liquid sample flow direction, indicates that a test is properly conducted and said sample contains no analyte or the analyte below detection level; or
   2) after a liquid sample containing an analyte at or above detection level flows laterally along said test device and passes said plurality of reagent dots, said plurality of reagent dots:
      a) form two separate two-dimensional signal features A and B and an additional signal feature C, said feature A, feature B or a combination thereof, viewed from a direction substantially parallel or opposite to the liquid sample flow direction, indicates that a test is properly conducted, and a combination of one or both of said features A and B and said feature C, viewed from a direction substantially parallel or opposite to the liquid sample flow direction, generates a signal that aids interpretation of the test result; and
      b) form at least one additional two-dimensional signal feature E, and a combination of at least one of said features A and B and said feature E, viewed from a direction substantially perpendicular to the liquid sample flow direction, indicates that said sample contains said analyte at or above detection level.

11. The test device of claim 10, wherein the plurality of reagent dots form at least two additional two-dimensional signal features E and E', and a combination of one of the features A and B and the features E and E', viewed from a direction substantially perpendicular to the liquid sample flow direction, indicates that the sample contains the analyte at or above detection level.

12. The test device of claim 11, wherein at least one, some or all of the features A-E', or a combination thereof, comprises a predetermined pattern that is selected from the group consisting of a line, multiple lines, a symbol, a geometric shape and an alpha-numeric shape.

13. The test device of claim 12, wherein the alpha-numeric shape is a letter, a word, a number or a combination thereof.

14. The test device of claim 13, wherein the combination of the features A and B, viewed from a direction substantially parallel or opposite to the liquid sample flow direction, forms the word "NO".

15. The test device of claim 13, wherein the combination of one of the features A and B and the features E and E', viewed from a direction substantially perpendicular to the liquid sample flow direction, forms the phrase "POS".

16. The test device of claim 13, wherein the combination of the features A, B and C forms the word "NOW".

17. The test device of claim 1, wherein the matrix comprises, at the locations for generating features A and/or B, a control reagent.

18. The test device of claim 1, wherein the matrix comprises, at the locations for generating features C, E, and/or E and E', a test reagent.

19. The test device of claim 1, wherein the plurality of reagent dots comprises at least 3, 4, 5, 6, 7, 8, 9, 10, 20, 30, 40, 50, 60, 70, 80, 90, 100, 500, 1,000, 5,000, 10,000 or more reagent dots.

20. The test device of claim 1, wherein at least a quarter, a third, half or all reagent dots do not overlap and are sufficiently spaced apart from each other so that when the liquid sample flows laterally along the matrix, flow of the liquid sample to, through and/or around one of the reagent dots does not substantially affect flow of the liquid sample to, through and/or around the other reagent dots.

21. The test device of claim 1, wherein at least one of the reagent dots has a diameter of about 0.1-1 um, 1-10 um, 10-50 um, 51-100 um, 101-200 um, 201-300 um, 301-400 um, 401-500 um and 501-1000 um, or at least one of the reagent dots has a diameter or surface area that is about 10%, 5%, 1%, 0.5%, 0.1%, 0.05%, 0.01%, 0.001% or smaller diameter or surface area of the length, width or surface area of the matrix.

22. The test device of claim 1, wherein the distance between edges of at least two of the reagent dots is about 1-10 um, 10-50 um, 51-100 um, 101-200 um, 201-300 um, 301-400, 401-500, or 501-600 um.

23. A method for detecting an analyte in a liquid sample, which method comprises:
   a) contacting a liquid sample with the test device of claim 1, wherein the liquid sample is applied to a site of the test device upstream of the plurality of reagent dots;
   b) transporting an analyte, if present in the liquid sample, and a labeled reagent to the plurality of reagent dots; and
   c) assessing the presence, absence, amount and/or pattern of signal(s) generated by the labeled reagent at the plurality of reagent dots to determining the presence, absence and/or amount of the analyte in the liquid sample.

24. The method of claim 23, wherein the liquid sample and the labeled reagent are premixed to form a mixture and the mixture is applied to the test device.

25. The method of claim 23, wherein the test device comprises a dried labeled reagent before use and the dried labeled reagent is solubilized or resuspended, and transported to the plurality of reagent dots by the liquid sample.

26. The method of claim 23, wherein the liquid sample is body fluid sample.

* * * * *